United States Patent
Vreugde et al.

(10) Patent No.: US 11,590,075 B2
(45) Date of Patent: Feb. 28, 2023

(54) METHODS AND PRODUCTS FOR REDUCING ADHESIONS

(71) Applicant: The University of Adelaide, Adelaide (AU)

(72) Inventors: Sarah Vreugde, North Brighton (AU); Peter John Wormald, North Adelaide (AU)

(73) Assignee: The University of Adelaide, Adelaide (AU)

( * ) Notice: Subject to any disclaimer, the term of this patent is extended or adjusted under 35 U.S.C. 154(b) by 0 days.

(21) Appl. No.: 16/489,115

(22) PCT Filed: Feb. 27, 2018

(86) PCT No.: PCT/AU2018/050167
§ 371 (c)(1),
(2) Date: Aug. 27, 2019

(87) PCT Pub. No.: WO2018/152592
PCT Pub. Date: Aug. 30, 2018

(65) Prior Publication Data
US 2020/0038321 A1 Feb. 6, 2020

(30) Foreign Application Priority Data
Feb. 27, 2017 (AU) ................. 2017900650

(51) Int. Cl.
| | | |
|---|---|---|
| *A61K 9/06* | (2006.01) | |
| *A61K 31/4412* | (2006.01) | |
| *A61K 47/36* | (2006.01) | |
| *A61K 9/00* | (2006.01) | |
| *A61L 31/04* | (2006.01) | |
| *A61L 31/14* | (2006.01) | |
| *A61L 31/16* | (2006.01) | |
| *A61P 41/00* | (2006.01) | |

(52) U.S. Cl.
CPC ............ *A61K 9/06* (2013.01); *A61K 31/4412* (2013.01); *A61K 47/36* (2013.01)

(58) Field of Classification Search
CPC .. A61K 31/4412; A61K 47/36; A61K 9/0014; A61K 9/06; A61P 41/00
See application file for complete search history.

(56) References Cited

U.S. PATENT DOCUMENTS

| | | | | |
|---|---|---|---|---|
| 8,809,301 B2 * | 8/2014 | Athanasiadis | ........ | A61L 26/008 514/55 |
| 2005/0106230 A1 * | 5/2005 | Young | ................. | A61K 9/0004 424/450 |
| 2010/0092546 A1 * | 4/2010 | Gurtner | ............... | A61K 9/0014 424/449 |

FOREIGN PATENT DOCUMENTS

| | | |
|---|---|---|
| CN | 101822643 | 5/2012 |
| EP | 1364645 | 11/2003 |
| WO | WO 2006/032143 | 3/2006 |
| WO | WO 2007/120818 | 10/2007 |
| WO | WO 2013/075015 | 5/2013 |
| WO | WO 2016/130485 | 8/2016 |

OTHER PUBLICATIONS

Zhang et al.; Sci Transl Med. Jun. 3, 2015; 7(290): 290ra92.*
Aziz et al.; Antimicrobial Agents and Chemotherapy; Jan. 2012; vol. 56, No. 1; pp. 280-287; published ahead of print Oct. 24, 2011.*
Hegasy Illustration "How Cells Sense and Adapt to Oxygen Availability." (https://upload.wikimedia.org/wikipedia/commons/5/5b/HIF_Nobel_Prize_Physiology_Medicine_2019_Hegasy_ENG.png); downloaded Apr. 10, 2020.*
NPL Google search for postoperative adhesion and iron chelation; (2-pg pdf); downloaded Apr. 10, 2020.*
Kontoghiorghes et al.; Hemoglobin, 34(3); pp. 227-239; published Jun. 2010. Available Dec. 2008.*
Atilgan et al., "Evaluation of Vitamin C and Vitamin E for Prevention of Postoperative Adhesion: A Rat Uterine Horn Model Study," *J. Obstet. Gynaecol. Res.*, vol. 41:418-423, 2015.
Binda et al., "Prevention of Adhesion Formation in a Laparoscopic Mouse Model should Combine Local Treatment with Peritoneal Cavity Conditioning," *Hum. Reprod.*, vol. 24:1473-1479, 2009.
Güney et al., "Effects of Quercetin and Surgicel for Preventing Adhesions after Gynecological Surgery: A Rat Uterine Horn Model," *J. Obstet. Gynaecol. Res.*, vol. 43:179-184, 2017.
Shin et al., "PLGA Nanofiber Membranes Loaded with Epigallocatechin-3-O-Gallate are Beneficial to Prevention of Postsurgical Adhesions," *Int. J. Nanomedicine*, vol. 9:4067-4078, 2014.
Yuzbasioglu et al., "The Effect of Intraperitoneal Catalase on Prevention of Peritoneal Adhesion Formation in Rats," *J. Invest. Surg.*, vol. 21:65-69, 2008.
Zhang et al., "Controlled Release of Curcumin from Curcumin-Loaded Nanomicelles to Prevent Peritendinous Adhesion during Achilles Tendon Healing in Rats," *Int. J. Nanomedicine*, vol. 11:2873-2881, 2016.
Goncalves et al., "Deferiprone targets aconitase: implication for Friedreich's ataxia treatment," *BMC Neurol* 8:20, 2008.
Merkel et al., "Decreased Iron Overload and Oxidative Stress in Transfusion Dependent Patients with Myelodysplastic Syndromes (MDS) with the Oral Iron Chelator Deferiprone," *Blood* 132(S1):4381, 2018.

(Continued)

*Primary Examiner* — Jeffrey T. Palenik
(74) *Attorney, Agent, or Firm* — Klarquist Sparkman, LLP

(57) ABSTRACT

The present disclosure relates to methods and products for reducing adhesions. In certain embodiments, the present disclosure provides a method of reducing adhesions in a subject, the method comprising exposing a region in the subject susceptible to formation of an adhesion to an agent having iron chelation and/or antioxidant activity, thereby reducing adhesions in the subject.

7 Claims, 8 Drawing Sheets

(56) References Cited

OTHER PUBLICATIONS

Mittal et al., "Reactive oxygen species in inflammation and tissue injury," *Antioxid Redox Signal* 20(7):1126-1167, 2014.
Mohammadpour et al., "Wound healing by topical application of antioxidant iron chelators: kojic acid and deferiprone," *Int Wound J* 10(3):260-264, 2013.
Ten Raa et al., "The role of neutrophils and oxygen free radicals in post-operative adhesions," *J Surg Res* 136, 45-52, 2006.

\* cited by examiner

METHODS AND PRODUCTS FOR REDUCING ADHESIONS

PRIORITY CLAIM

This application is the U.S. National Stage of International Application No. PCT/AU2018/050167, filed on Feb. 27, 2018, which was published in English under PCT Article 21(2), which claims priority to Australian Provisional Patent Application No. 2017900650, filed on Feb. 27,2017, the entire content of which is hereby incorporated by reference.

FIELD

The present disclosure relates to methods and products for reducing adhesions.

BACKGROUND

Adhesions are fibrous bands that form between tissues and organs which are not normally connected. They typically form when two or more surfaces, such as the surfaces of discrete tissues, stick together following injury associated with surgery. Adhesions are a frequent complication of surgical procedures and their formation is difficult to avoid.

Whilst normal wound healing is a highly regulated and coordinated process, the causes underlying formation of adhesions are complex and not completely understood. In addition, the formation of adhesions can be exacerbated by a number of pathological processes. The critical time interval to block formation of many types of adhesions appears to be in the first 48 hours after initial injury, and the extent of adhesion formation appears to be dependent, at least in part, on the inhibition of fibroblast proliferation and/or migration during that time.

Adhesions may occur after almost all types of surgeries and are capable of forming in most anatomical locations. For example, a bowel resection within the abdominal cavity may lead to attachment between the bowel and the abdominal wall. Adhesions can produce pain and discomfort for the patient, impair the functioning of effected organs, and hinder subsequent surgeries in the same anatomical region. Adhesions are also a common complication of spinal surgery, and they are a primary reason for postoperative pain even after a successful spinal surgery.

The formation of adhesions may result in increased health care costs. These costs include subsequent surgeries to remove or separate adhesions, additional visits to medical practitioners, pain medication and lost productivity. In addition, if a patient has a subsequent operation at the same surgical site, the operation can be complicated by existing adhesions. Surgeons may have to spend additional time removing existing adhesions before a new procedure can begin.

As such, the reduction of adhesions remains an important goal of surgical practice. A variety of approaches have been undertaken to treat adhesions, but they have not generally withstood rigorous clinical examination or they have significant practical limitations.

For example, one such approach is to perform a further operation to remove existing adhesions. However, many times these operations are not effective because adhesions simply reform. Another approach to preventing adhesions has been the use of agents such as anti-inflammatory agents, anticoagulants, and fibrinolytic agents. However, such approaches have not been particularly encouraging.

Another approach has been the development of barriers to be used in surgical procedures, with the aim of physically separating tissues. Liquid barriers and gels typically do not perform well, and structural barriers have been found to have lower clinical effectiveness than desired.

Accordingly, there is a need for new methods and products to reduce the formation of adhesions.

SUMMARY

The present disclosure relates to methods and products for educing adhesions.

Certain embodiments of the present disclosure provide a method of reducing adhesions in a subject, the method comprising exposing a region in the subject susceptible to formation of an adhesion to an agent having iron chelation and/or antioxidant activity, thereby reducing adhesions in the subject.

Certain embodiments of the present disclosure provide a method of reducing adhesions in a subject, the method comprising applying a composition comprising an agent having iron chelation and/or antioxidant activity to a region susceptible to formation of an adhesion in the subject, thereby reducing adhesions in the subject.

Certain embodiments of the present disclosure provide a method of reducing surgical adhesions in a subject, the method comprising applying a composition comprising an agent having iron chelation and/or antioxidant activity to a region susceptible to formation of a surgical adhesion in the subject, thereby reducing surgical adhesions in the subject.

Certain embodiments of the present disclosure provide a method of reducing postoperative adhesions in a subject, the method comprising applying a composition comprising an agent having iron chelation and/or antioxidant activity to a region susceptible to formation of a postoperative adhesion in the subject, thereby reducing postoperative adhesions in the subject.

Certain embodiments of the present disclosure provide a method of preventing and/or treating a subject for an adhesion, the method comprising applying a composition comprising an agent having iron chelation and/or antioxidant activity to a region susceptible to formation of an adhesion in the subject, thereby preventing and/or treating the subject for an adhesion.

Certain embodiments of the present disclosure provide a method of treating a subject for an adhesion, the method comprising:
  (i) performing an adhesiolytic procedure on the subject; and
  (ii) applying a composition comprising an agent having iron chelation and/or antioxidant activity to a region susceptible to formation of an adhesion following the adhesiolytic procedure to reduce formation of a new adhesion in the subject,
thereby treating the subject for the adhesion.

Certain embodiments of the present disclosure provide use of an agent having iron chelation and/or antioxidant activity to reduce adhesions in a subject.

Certain embodiments of the present disclosure provide an agent having iron chelation and/or antioxidant activity for use in the treatment of adhesions.

Certain embodiments of the present disclosure provide an anti-adhesion composition comprising an agent having iron chelation and/or antioxidant activity.

Certain embodiments of the present disclosure provide a product for reducing adhesions in a subject, the product comprising the following components:

(i) an agent having iron chelation and/or antioxidant activity; and/or
(ii) one or more components for forming a gel comprising an agent having iron chelation and/or antioxidant activity, the gel being suitable for application to a surgical site; and/or
(iii) a pre-formed gel comprising an agent having iron chelation and/or antioxidant activity, wherein the gel is suitable for application to a surgical site; and optionally:
(a) an applicator for dispensing gel comprising the agent to a surgical site; and/or
(b) instructions for forming the gel and/or dispensing the gel to a surgical site.

Certain embodiments of the present disclosure provide a nasal and/or sinus rinse composition comprising an agent having iron chelation and/or antioxidant activity and a liquid carrier.

Certain embodiments of the present disclosure provide a chitosan based gel comprising an agent having iron chelation and/or antioxidant activity.

Certain embodiments of the present disclosure provide an anti-adhesion composition comprising a chitosan based gel and an agent having iron chelation and/or antioxidant activity.

Certain embodiments of the present disclosure provide a method of producing a product for reducing adhesions in a subject, the method comprising forming a gel comprising an agent having iron chelation and/or antioxidant activity, wherein the gel is suitable for application to a surgical site.

Certain embodiments of the present disclosure provide a method of identifying an agent for reducing adhesions, the method comprising determining the ability of an agent having iron chelation and/or antioxidant activity to reduce adhesions in a subject, thereby identifying the agent as an agent for reducing adhesions.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

DETAILED DESCRIPTION

Figure 1:
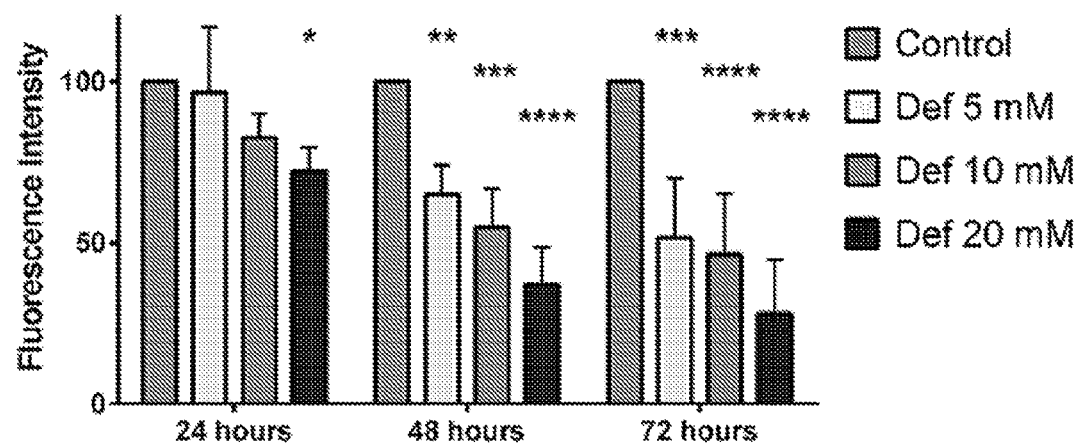
FIG. 1 shows fibroblast proliferation, normalised to control non-treated primary fibroblasts, measured using the Alamar Blue Proliferation assay, showing a dose and time-dependent significant reduction in fibroblast proliferation with deferiprone (Def) treatments. * p<0.05,  p<0.01, * p<0.001, **** p<0.0001.

The present disclosure relates to methods and products for reducing adhesions.

The present disclosure is based, at least in part, upon the recognition that agents with iron chelating and/or antioxidant activity are effective in reducing adhesions in subjects. Without being bound by theory, it has been demonstrated that the antioxidant and iron chelator deferiprone inhibits proliferation and migration of fibroblasts in vitro. In addition, it has been found that a gel based system can be used to provide maximum delivery of the agent to a surgical site within 48 hours, which is coincident with the critical period for blocking adhesion forming. This gel system with deferiprone reduces adhesions in vivo in a large animal laminectomy model.

Certain embodiments of the present disclosure provide a method of reducing adhesions in a subject.

In certain embodiments, the present disclosure provides a method of reducing adhesions in a subject, the method comprising exposing a region in the subject susceptible to formation of an adhesion to an agent having iron chelation and/or antioxidant activity, thereby reducing adhesions in the subject.

In certain embodiments, the subject is a human subject. For example, a human patient having undergone a surgical procedure may be treated so as to expose a region susceptible to formation of an adhesion to an agent having iron chelation and/or antioxidant activity.

In certain embodiments, the subject is an animal subject, a mammalian subject, a livestock animal (such as a horse, a cow, a sheep, a goat, a pig), a domestic animal (such as a dog or a cat) and other types of animals, such as monkeys, rabbits, mice, rats and laboratory animals. Veterinary applications of the present disclosure are contemplated. For example, post-operative abdominal adhesions are a significant problem in horses.

In certain embodiments, the subject is susceptible to the formation of adhesions.

In certain embodiments, the subject is suitable for treatment to reduce formation of adhesions.

In certain embodiments, the subject has an increased risk or likelihood of suffering from an adhesion. For example, a subject may have one or more risk factors associated with an increased risk of formation of post-operative adhesions, such as certain genetic polymorphisms, increased estrogen exposure, endometriosis, diabetes mellitus, metabolic syndrome, hyperglycemia, obesity, alcohol consumption, treatment with certain medications, hormone therapy, pregnancy, and cancer.

In certain embodiments, the subject is suffering from an existing adhesion. In certain embodiments, the subject is suffering from an existing adhesion and is suitable for an adhesiolytic procedure to remove the existing adhesion and subsequent treatment to reduce the formation of new adhesions.

In certain embodiments, the region in the subject susceptible to formation of an adhesion comprises a surgical site and/or a site overlapping, adjacent or near to a surgical site.

In certain embodiments, the region in the subject susceptible to formation of an adhesion comprises a non-surgical site. In certain embodiments, the region in the subject susceptible to formation of an adhesion is a site of inflammation.

In certain embodiments, the region in the subject susceptible to formation of an adhesion comprises a site where an existing adhesion has been removed or subject to an adhesiolytic procedure.

In certain embodiments, the method comprises reducing an adhesion at a surgical site, an adhesion formed at a non-surgical site, or an adhesion formed after the lysis of a previous adhesion.

In certain embodiments, the adhesion is an adhesion arising from a surgery.

Examples of surgery where an adhesion may form post-operatively include spinal surgery, such as laminectomy, disc decompression surgery, hemi-laminectomy, arthrodesis, microdiscectomy, discectomy, laminoplasty, rhizolysis and spinal tumuor removal; abdominal surgery or pelvic surgery, such as gastro-intestinal surgery, vascular surgery, renal surgery, urological surgery, gynaecological surgery, bowel surgery, hepatic surgery, liver transplant surgery, appendectomy, laparoscopy, laparotomy, gynecological adnexal surgery, endometriosis surgery, ovarian surgery, tubal surgery and fimbriae surgery; cardiac surgery, such as cardiac valve surgery, coronary bypass surgery, angioplasty, atherectomy, cardiomyoplasty, and heart transplant surgery; joint and tendon surgery, such as joint replacement or arthroplasty; sinus surgery, such as operative procedures on the paranasal sinuses, a skull base surgery, and skull base surgery involving tumour removal, lacrimal and orbital surgeries; plastic surgery, such as a surgical procedure involving prevention of fibrous capsule contractions on implants, such as breast implants.

In certain embodiments, the adhesion is an adhesion arising from spinal surgery, abdominal surgery, pelvic surgery, cardiac surgery, joint and tendon surgery, sinus surgery or plastic surgery. Other types of surgical procedures giving rise to adhesions are contemplated.

In certain embodiments, the spinal surgery comprises one of laminectomy, disc decompression surgery, hemi-laminectomy, arthrodesis, microdiscectomy, discectomy, laminoplasty, rhizolysis and spinal tumuor removal.

In certain embodiments, the abdominal surgery or pelvic surgery comprises one of gastro-intestinal surgery, vascular surgery, renal surgery, urological surgery, gynaecological surgery, bowel surgery, hepatic surgery, liver transplant surgery, appendectomy, laparoscopy, laparotomy, gynecological adnexal surgery, endometriosis surgery, ovarian surgery, tubal surgery, and fimbriae surgery.

In certain embodiments, the cardiac surgery comprises one of cardiac valve surgery, coronary bypass surgery, angioplasty, atherectomy, cardiomyoplasty, and heart transplant surgery.

In certain embodiments, the joint and tendon surgery comprises joint replacement or arthroplasty.

In certain embodiments, the sinus surgery comprises one of an operation on the paranasal sinuses, a skull base surgery, and a skull base surgery involving tumour removal, lacrimal and orbital surgeries.

In certain embodiments, the plastic surgery comprises a surgical procedure involving prevention of fibrous capsule contractions on implants, such as a breast implant.

In certain embodiments, the method reduces the formation, rate of formation, quantity or incidence of adhesions.

In certain embodiments, the method reduces the formation or quantity of adhesions by at least 10%, at least 20%, at least 30%, at least 40%, at least 50%, at least 60%, by at least 70%, by at least 80%, or by at least 90%. In certain embodiments, the method reduces the formation or quantity of adhesions by 20% or more, 30% or more, 40% or more, 50% or more, 60% or more, 70% or more, 80% or more, or 90% or more.

In certain embodiments, the method reduces a characteristic of an adhesion, such as the strength, thickness, extent, severity and/or vascularisation of an adhesion.

In certain embodiments, the method reduces the grading of an adhesion. For example, adhesions may be graded as filmy adhesions, strong adhesions, or very strong vascularised adhesions.

For abdominal adhesions, a standardized grading system is as follows: 0—no adhesions; 1—thin filmy adhesions; 2—more than one this adhesion; 3—thick adhesion with focal point; 4—thick adhesion with planar attachment; 5—very thick vascularised adhesions or more than one planar adhesions.

In certain embodiments, the method prevents the formation of adhesions.

Methods for assessing adhesions are known in the art, for example using grading systems as described herein.

In certain embodiments, the agent has iron chelation activity.

Methods for determining iron chelation activity are known in the art, for example in vitro methods for assessing the ability of an agent to bind iron, or methods for assessing the ability of an agent to bind iron in vivo. Iron chelators used in therapy are described, for example, in "Iron Chelation Therapy" (2012) Advances in Experimental Medicine and Biology, Volume 509; edited by Cairn Hersko; published by Springer US, Kluwer Academic/Plenum Publishers.

Examples of agents with iron chelation activity include deferiprone, deferoxamine, desferrioxamine, deferasirox, kojic acid, tetramic acid, desferrithiocin, 8-hydroxyquinoline analogues, clioquinol, O-trensox (tris-N-(2-aminoethyl-[8-hydroxyquinoline-5-sulfonato-7-carboxamido] amine), tachpyridine (N,N',N"-tris(2-pyridylmethyl)-cis,cis-1,3,5-thaminocyclohexane), Dexrazone, Thiosemicarbazones, Triapine® (3-aminopyridine-2-carboxaldehyde thiosemicarbazone [3-AP]), pyridoxal isonicotinoyl hydrazone (PIH) and its analogs, phytochemicals, proanthocvanidins, epicatechins, flavonols and anthocyanin, curcumin, apocyanin, kolaviron, floranol, nitrilotriacetate, pycnogenol, proevanidins, baicalein, baicalin, quercetin, tetramethylpyrazine, ferulic acid, ligustrazine, quercetin, chrysin, 3-hydroxyflavone, 3',4'-dihydroxy flavone, rutin and flavones, ferrozine, gallic acid, catechin, epigallocatechin gallate (EGCG) and proanthocyanidins, green tea catechins, black tea theallavins, ethylenediaminetetraacetic acid/ethylenediaminetetraacetate salts (EDTA), citric acid, phosphonic acid/phosphonates and its analogs, arninophosphonates and its analogs, hisphosphonates and its analogs; and/or an acceptable salt, derivative (such as a chemically substituted form), solvate, hydrate, tautomer, pro-drug, or stereoisomer of any of aforementioned. Other iron chelators are contemplated.

Iron chelating agents may be obtained commercially or synthesized by a method known in the art.

In certain embodiments, the agent has antioxidant activity.

Methods for determining antioxidant activity are known in the art, for example methods for assessing the ability of an agent to inhibit oxidation and/or assessing the ability of agents to remove oxidizing agents or free radicals, such as reactive oxygen species.

Examples of agents with antioxidant activity include small molecule compounds such as glutathione, bilirubin, ubiquinone, vitamin C, vitamin E, carotenoids, phytic acid, oxalic acid, tannins, beta-caroten, eugenol, retinol, cannabinoids, dithiol-containing antioxidants, lipoic acid, DTT (dithiothreitol), aspirin, salicylic acid, glutathione, ovothiol and phenolic compounds, and enzymes such as SOD, GPX, PRDX, and catalase. Other agents with antioxidant activity are contemplated.

Antioxidant agents may be obtained commercially or synthesized by a method known in the art.

In certain embodiment, the agent has both iron chelation and antioxidant activity.

In certain embodiments, the agent having iron chelation and/or antioxidant activity comprises a reactive oxygen species inhibitor. In certain embodiments, the reactive oxygen species inhibitor comprises a scavenger of reactive oxygen species and/or an inhibitor of generation of reactive oxygen species. Methods for determining the ability of an agent to act as a ROS inhibitor are known in the art, for example as described in Pavelescu et al. (2015) *J. Med. Life* 8: 38-42, and Woolley et al. (2013) *Trends Biochem Sci* (11): 556-565.

In certain embodiments, the agent comprises one or more of deferiprone, deferoxamine and desferrioxamine, or any combination thereof. These agents may be obtained commercially or synthesized by a method known in the art. For example deferiprone may be obtained from Apotex Pty Ltd or Selleckchem.com (Product #S4067) and desferrioxamine (as the mesylate salt) may be obtained from Merck (formerly Sigma-Aldrich; Product. #D9533).

In certain embodiments, the agent comprises deferiprone.

The term "exposing", and related terms such as "expose" and "exposure", as used herein refers to directly and/or indirectly contacting and/or treating a region susceptible to formation of an adhesion to an agent having iron chelation and/or antioxidant activity.

The agent may be exposed to the region in the subject in a suitable form. In this regard, the agent may also be a pro-form of the agent, or a derivative that will form a therapeutically effective form of the agent when exposed to a subject.

In certain embodiments, the method comprises contacting the region with the agent. In certain embodiments, the method comprises applying the agent to the region, such as by coating the region with the agent, spraying the region with the agent, or by applying a composition comprising the agent to the region. For example, in the case of sinus surgery, a composition may be applied to the surgical site and/or a composition can be used to rinse the sinuses postoperatively.

In certain embodiments, the exposure to the agent utilises a therapeutically effective amount of the agent. The term "therapeutically effective amount" as used herein refers to that amount of an agent that is sufficient to reduce adhesions, or to prevent and/or treat adhesions. The therapeutically effective amount will vary depending upon a number of factors, including for example the specific activity of the agent being used, clinical characteristics, age, physical condition, existence of other disease states, and nutritional status of the subject. Examples of therapeutic amounts are as described herein.

Formulations for delivery of agents having iron chelation and/or antioxidant activity are described for example in Remington: The Science and Practice of Pharmacy, edited by David B. Troy and Paul Beringer (2006) Lipincott Williams & Wilkins, and Tiwari G. et al (2012) *Int. J. Phar. Investig* 2(1):2-11;

In certain embodiments, the amount of the agent delivered is in an amount ranging from one of the following selected ranges: 1 µg to 100 mg; 1 µg to 10 mg; 1 µg to 1 mg; 1 µg to 100 µg; 1 µg to 10 µg; 10 µg to 100 mg; 10 µg to 10 mg; 10 µg to 1 mg; 10 µg to 100 µg; 100 µg to 100 mg; 100 µg to 10 mg; 100 µg to 1 mg; 1 mg to 10 mg; 1 mg to 100 mg and 10 mg to 100 mg. The dose and frequency of delivery may be determined by one of skill in the art.

In certain embodiments, the amount of the agent delivered is in an amount ranging from 1 mg to 100 mg.

In certain embodiments, the exposure to the agent is a prophylactic exposure. In certain embodiments, the exposure to the agent comprises exposure to the agent before an adhesion has formed and/or during adhesion formation.

In certain embodiments, the exposure of the agent to the region comprises delivery of the agent by way of a gel, an ointment, a cream, a lotion, a foam, an emulsion, a suspension, a spray, an aerosol, a solution, a liquid, a powder, a semi-solid, a gel, a solid, a paste, or a tincture.

In certain embodiments, the exposure of the agent comprises delivery of the agent by way of particles, such as microparticles or nanoparticles, or delivery by way of liposomes.

Other forms of delivery of the agent comprises delivery by way of a scaffold, such as a biomaterial scaffold including a scaffold produced from collagen, hydroxyapatite, ß-tricalcium phosphate or a combination thereof. Methods for incorporating agents into such substrates are known in the art.

In certain embodiments, the method comprises applying a composition, formulation or medicament comprising an agent as described herein to the region susceptible to formation of an adhesion in the subject. A composition, formulation or medicament may include additional numerous various excipients, dosage forms, and other components that are suitable for use in connection with the delivery of the agent, and may be in a form such as solid form, a semi-solid form, a liquid form, or a foam form.

In certain embodiments, the method comprises applying a composition comprising the agent to the region susceptible to formation of an adhesion in the subject. Methods for producing compositions are known in the art, for example as described in Remington: The Science and Practice of Pharmacy, edited by David B. Troy and Paul Beringer (2006) Lipincott Williams & Wilkins, and Tiwari G. et al (2012) *Int. Phar. Investig* 2(1)2-11;

In certain embodiments, the composition comprises one or more of a gel, a solution, a rinse, an emulsion, a cream, a spray, nanoparticles, microparticles, liposomes, an ointment, a cream, a lotion, a foam, a suspension, an aerosol, a liquid, a powder, a semi-solid, a solid, a paste, or a tincture.

Gels are semisolid systems, and typically are made up of dispersions of molecules in a liquid vehicle rendering jelly-like through the addition of a gelling agent.

Solutions are liquid preparations of soluble chemicals dissolved in solvents, such as water, alcohol, or propylene glycol. For example, a nasal rinse comprising the agent may be used for reducing inflammation or adhesions in the sinuses.

Emulsions are two-phase preparations in which one phase (the dispersed or internal phase) is finely dispersed in the other (continuous or external phase). The dispersed phase can have either a hydrophobic-based (oil-in-water), or be aqueous based (water-in-oil). Emulsions may include water-in-oil emulsions or oil-in-water emulsions.

Creams are medicaments dissolved or suspended in water removable or emollient bases. Creams are typically classified as water-in-oil or oil-in-water. Lotions are typically clear/semi-clear solutions. Lotions typically contain 25-50% alcohol and may also contain an antiseptic, an emollient, and a haemostypic substance. Ointments are semi-solid preparations. Water-soluble ointments may be formulated for example with polyethylene glycol. Pastes are ointments into which a high percentage of insoluble solids have been added, typically up to 50% by weight.

Powders typically utilize small particle sizes which have a large surface area per unit weight.

Foams typically utilize trapped gas in liquid, semi-solid Or solid bases.

In certain embodiments, the composition is a gel. Examples of gel compositions include fibrin gels, polysaccharide gels (such as an alginate, an agarose, a chitosan, Or a pectate), polymer gels (such as a polyvinyl alcohol polymer), and protein gels (such as a gelatin, or collagen). Methods for producing gels are known in the art.

In certain embodiments, the composition comprises a hydrogel. Methods for producing hydrogels are known in the art, for example are as described in Gulrez et al. (2011) "Hydrogels: Methods of Preparation, Characterisation and Applications" edited by Angelo Carpi, ISBN 978-953-307-268-5.

In certain embodiments, the gel comprises one or more of a chitosan, a dextran, a carbohydrate polymer, a hyaluronic acid and/or a salt thereof, a collagen, a carboxymethylcellulose, a gelatine, a polyacylate, and an alginate.

In certain embodiments, the composition comprises a chitosan-based gel. Chitosan based gels are known in the art, for example as described in international patent application WO/2009028965 and Ahmad et al. (2015) *Res Pharm Sci* 10(1): 1-16.

In certain embodiments, the agent is exposed to the region by administering the agent to the subject.

The agent as described herein may be administered to the subject in a suitable form. In this regard, the terms "administering" or "providing" include administering the agent(s), or administering a prodrug of the agent(s), or a derivative of the agent(s) that will form a therapeutically effective amount of the agent(s) within the body of the subject. The terms include for example routes of administration that are systemic (e.g., via injection such as intravenous injection, orally in a tablet, pill, capsule, or other dosage form useful for systemic administration of pharmaceuticals), and topical (e.g., creams, solutions, gels and the like, and also solutions such as mouthwashes, and rinses for topical oral administration).

Methods for administering agents are known in the art.

The agent may be administered alone or may be delivered in a mixture with other therapeutic substances and/or other substances that enhance, stabilise or maintain the activity of the agent(s). In certain embodiments, an administration vehicle (e.g., pill, tablet, implant, injectable solution, etc.) contains the agent(s) and/or additional substance(s).

When administered to a subject, the effective dosage may vary depending upon the particular agent(s) utilized, the mode of administration, as well as various physical factors related to the subject being treated. The daily dosages are expected to vary with route of administration, and the nature of the agent(s) administered.

In certain embodiments, the agent(s) is administered orally. In certain embodiments, the agent(s) is administered topically. In certain embodiments, the agent(s) is administered via injection, such as intravenous injection. In certain embodiments, the agent(s) is administered parenterally. In certain embodiments, the agent(s) is administered by direct introduction to the lungs, such as by aerosol administration, by nebulized administration, and by being instilled into the lung. In certain embodiments, the agent(s) is administered by implant. In certain embodiments, the agent(s) is administered by subcutaneous injection, intraarticularly, rectally, intranasally, intraocularly, vaginally, or transdermally. In certain embodiments, the agent(s) is administered by a biological or non-biological implant.

"Intravenous administration" is the administration of substances directly into a vein. In certain embodiments, the agent may also be administered intravenously. Compositions containing the agent as described herein suitable for intravenous administration may be formulated by a skilled person, and typically contain a carrier or excipient, such as isotonic saline.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical forms for oral administration of therapeutic substances includes the use of tablets or capsules.

In certain embodiments it may be desirable to administer the agent(s) directly to the airways in the form of an aerosol. Formulations for the administration of aerosol forms are known.

In certain embodiments, the agent(s) may also be administered parenterally (such as directly into the joint space) or intraperitoneally. For example, solutions or suspensions of the agent(s) in a non-ionised form or as a pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations typically contain a preservative to prevent the growth of microorganisms.

In certain embodiments, the agent(s) may also be administered by injection. Pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol and liquid polyethylene glycol), suitable mixtures thereof, and vegetable oils.

For example, a pharmaceutical composition for intravenous use of an iron chelator may be as follows: 10-500 mg of deferiprone in isotonic saline, optionally including one or more pharmaceutically acceptable additives and/or excipients.

In certain embodiments, the agent(s) may also be administered transdermally. Transdermal administrations are understood to include all administrations across the surface of the body and the inner linings of bodily passages including epithelial and mucosal tissues. Such administrations may be carried out using the agent as described herein, or pharmaceutically acceptable salts thereof, in lotions, creams, foams, patches, suspensions, solutions, and suppositories (rectal and vaginal).

Transdermal administration may also be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient.

In certain embodiments, the agent(s) may also be administered by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the agent(s) may be administered or delivered by way of solid or semi-solid substrate, for example being incorporated into a matrix, a scaffold or a support, such as a biodegradable matrix or support. Methods for delivering agents) via scaffolds are known in the art. For example, a biomaterial scaffold including a scaffold produced from collagen, hydroxyapatite, β-tricalcium phosphate or a combination thereof may be used to deliver the agent. Methods for incorporating agents into such substrates are known in the art.

In certain embodiments, the agent(s) may be administered or delivered by way of an implantable composition. Methods for preparing implantable compositions are known in the art.

Additional numerous various excipients, dosage forms, dispersing agents and the like that are suitable for use in connection with the administration of the agent and/or the formulation into compositions, medicaments, or pharmaceutical compositions are contemplated.

Formulations are known and described in, for example, Remington's Pharmaceutical Sciences, 17th ed., Mack Publishing Company, Easton, Pa., 1985, which is incorporated herein by reference in its entirety.

In certain embodiments, a composition as described herein comprises a desired release characteristic.

Formulations for controlling the release of active agents, such as immediate release formulations, sustained release formulations and delayed release formulations, are known in the art, for example as described in "Handbook of Pharmaceutical Controlled Release Technology" edited by Donald L Wise (2000) Marcel Dekker Inc., 270 Madison Avenue New York, N.Y. 10016. For example, immediate release formulations may utilise the agent for immediate release in a disintegrant such as like cross linked carboxymethylcellulose, a sodium starch glycolate or a polyvinylpyrrolidone which provide rapid disintegration of a tablet, and delayed release formulations may utilise the delayed release agent (eg the non-iron metalloporphyrin) in a pH dependent coating of an agent using an acrylic based resin such as Eudragit S (methacrylic copolymer B, NF) and/or Eudragit L (methacrylic copolymer A, NF).

In certain embodiments, the composition comprise an amount of the agent ranging from one of the following selected ranges: 1 µg/ml to 100 mg/ml; 1 µg/ml to 10 mg/ml; 1 µg/ml to 1 mg/ml; 1 µg/ail to 100 µg/ml; 1 µg/ml to 10 µg/ml; 10 µg to 100 mg/ml; 10 µg/ml to 10 mg/ml; 10 µg/ml to 1 mg/ml, 10 µg/ml to 100 µg/ml; 100 µg/ml to 100 mg/ml; 100 µg/ml to 10 mg/ml; 100 µg/ml to 1 mg/ml, 1 mg/ml to 10 mg/ml; 1 mg/ml to 100 mg/ml and 10/ml mg to 100 mg/mi. Other ranges are contemplated.

In certain embodiments, the composition comprises an amount of the agent in the range from 1 mg/ml to 100 mg/ml.

In certain embodiments, the composition comprises an amount of deferiprone in the range from 1 mg/ml to 100 mg/ml.

In certain embodiments, the composition comprise a concentration of the agent ranging from one of the following selected ranges: 1 µM to 1 M; 1 µM to 100 mM; 1 µM to 10 mM; 1 µM to 1 mM; 1 µM to 100 mM; 10 µM to 10 µM; 10 µM to 1 M; 10 µM to 100 mM; 10 µN to 10 mM; 10 µM to 1 mM; 10 µM to 100 µM; 100 µM to 1M; 100 µM to 100 mM; 100 µM to 10 mM; 100 µM to 1 mM; 1 mM to 1 M; 1 mM to 100 mM; 1 mM to 10 mM; 10 mM to 1 M; 10 mM to 100 mM; and 100 mM to 1 M. Other ranges are contemplated.

In certain, the composition comprises a concentration of deferiprone in a range from one of the following selected ranges: 1 mM to 1 M, 1 mM to 100 mM, 1 mM to 10 mM, 10 mM to 1 M, 10 mM to 100 mM, or 100 mM to 1 M.

In certain embodiments, the agent is one or more of deferiprone, deferoxamine and/or desferrioxamine, or any combination thereof. Other agents are as described herein.

In certain embodiments, the composition comprises a concentration of deferiprone of 1 mM or greater, 2 mM or greater, 3 mM or greater, 4 mM or greater, 5 mM or grater, 10 mM or greater, 20 mM or greater, 30 mM or greater, 40 mM or greater, 50 mM or greater, 100 mM or greater, 250 mM or greater, or 500 mM or greater.

In certain embodiments, the composition comprises a concentration of deferiprone of 1 mM or less, 2 mM or less, 3 mM or less, 4 mM or less, 5 mM or less, 10 mM or less, 20 mM or less, 30 mM or less 40 mM or less, 50 mM or less, 100 mM or less, 250 mM or less, 500 mM or less, or 1 M or less.

In certain embodiments, the composition comprises a concentration of deferiprone of 200 mM or less.

In certain embodiments, the composition comprises a concentration of deferiprone of 80 mM or less.

In certain embodiments, the composition comprises a concentration of deferiprone of 50 mM or less. In certain embodiments, the composition comprises a concentration of deferiprone of 20 mM or less. In certain embodiments, the composition comprises a concentration of deferiprone of 10 mM or less.

In certain embodiments, the composition provides greater than 90% release of the agent within 96 hours. In certain embodiments, the composition provides greater than 90% release of the agent within 72 hours. In certain embodiments, the composition provides greater than 90% release of the agent within 48 hours. In certain embodiments, the composition provides greater than 80% release of the agent within 24 hours.

Methods for determining release rates of agents are known in the art.

In certain embodiments, the composition provides a release of the agent of up to a period of 14 days, up to a period of 7 days, up to a period of 3 days, up to a period of 2 days, or up to a period of 1 day.

In certain embodiments, the composition provides a release of the agent of at least of 14 days, at least 7 days, at least 3 days, at least 2 days, or at least 1 day.

In certain embodiments, the composition provides a release of the agent over a period of 1 to 14 days, 1 to 7 days, 1 to 3 days, or 1 to 2 days.

In certain embodiments, the composition provides a sustained release of the agent over a period of 0 to 14 days, 1 to 14 days, 2 to 14 days, 3 to 14 days, or 7 to 14 days. In certain embodiments, the composition provides a sustained release of the agent over a period of 3 to 14 days.

In certain embodiments, the composition is an immediate release composition. In certain embodiments, the composition is a sustained release composition. In certain embodiments, the composition is a controlled release composition. In certain embodiments, the composition is a delayed release composition. In certain embodiments, the composition is a slow release composition.

Formulations for controlling the release of active agents, such as immediate release formulations, sustained release formulations, slow release and delayed release formulations are known in the art, for example as described in "Handbook of Pharmaceutical Controlled Release Technology" edited by Donald L Wise (2000) Marcel Dekker Inc., 270 Madison Avenue New York, N.Y. 10016.

In certain embodiments, an active agent may be incorporated in a particle, and which provides sustained release of the agent. For example, sustained release particles may include a PLGA (poly lactic glycolic acid).

In certain embodiments, the method comprises further exposing the region susceptible to the formation to an antibiotic. Methods for exposing are as described herein.

Examples of antibiotics include aminoglycosides, carbapenems, cephalosporins, glycopeptides, lincoasmides, lipopeptides, macrolides, monobactams, nitrofurans, oxazolidinones, penicillins, peolypeptides, quinolones, fluoroquinones, sulphonamides, and tetracyclines. Antibiotics are commercially available, and methods for their use are known in the art, for example as described in "Therapeutic Guidelines—Antibiotic", Version 15, 2014, published by eTG complete.

For example, specific antibiotics include one or more of mupirocin, ciprofloxacin, ampicillin, amoxycillin, gentamicin, clavulanate, clindamycin, trimethoprim-sulfamethoxazole, doxycycline, minocycline, rifampin, linezolid, flucloxacillin, dicloxacillin, cefazolin, cephalothin and cephalexin, clindamycin, lincomycin, erythromycin, rifaximin, levofloxacin, sulbactam, cetoxitin, levofloxacin plus clindamycin or metronidazole, aztreonam, polymyxin E, metronidazole, ampicillin, and amoxicillin, ticarcillin and piperacillin, or in combination with a ß-lactamase inhibitor, such as clavulanic acid, sulbactam, or tazobactam. Other types of antibiotic are contemplated.

In certain embodiments, the antibiotic comprises one or more of mupirocin, gentamicin, doxycycline, metronidazole, amoxicillin, piperacillin, ciprofloxacin, trimethoprim-sulfamethoxazole (Bactrim), or any combination thereof.

In certain embodiments, the method comprises reducing adhesions arising from abdominal surgery and further exposing the region to one or more antibiotics as described herein.

In certain embodiments the method comprises reducing adhesions arising from sinus surgery and further exposing the region to one or more antibiotics as described herein.

In certain embodiments, a composition as described herein further comprises an antibiotic. In certain embodiments, a gel composition as described herein further comprises an antibiotic. Antibiotics are as described herein.

In certain embodiments, a composition for reducing adhesions arising from abdominal surgery further comprises one or more antibiotics as described herein.

In certain embodiments, a composition for reducing adhesions arising from sinus surgery further comprises one or more antibiotics as described herein.

In certain embodiments, the method comprises further exposing the region to an anti-inflammatory agent. Methods for use of anti-inflammatory agents are known in the art. Anti-inflammatory agents are commercially available or may be synthesized by a method known in the art.

In certain embodiments, the method further comprises exposing the region to a non-steroidal anti-inflammatory drug/agent.

Examples of non-steroidal anti-inflammatory drugs include agents such as retinoic acid, quinacrine, dipyridamole, aspirin (eg Disprin), ibuprofen (eg Nurofen), naproxen (eg Naprosyn), diclofenac (eg Voltaren) and celecoxib (eg Celebrex) indomethacin, oxaprozin, and piroxicam.

In certain embodiments, the method further comprises exposing the region to a corticosteroid.

Examples of corticosteroids include fluticasone propionate, fluticasone furoate, mometasone furoate, ciclesonide triamcinolone acetonide, flunisolide, beclomethasone, budesonide, and dexamethasone.

In certain embodiments, the method comprises further exposing the region to budesonide. For example, the method may further comprise exposing the region to budesonide in a gel composition.

In certain embodiments, a composition as described herein further comprises an anti-inflammatory agent, such as a corticosteroid.

In certain embodiments, a gel composition as described herein further comprises an anti-inflammatory agent.

In certain embodiments, the method comprises further exposing the region to an agent that is an iron mimetic and/or a heme mimetic. The term "iron mimetic" refers to an agent that is an analogue of iron and interferes with the action of iron in cells, including interfering with enzymes utilising iron, such as redox enzymes, or interferes with iron metabolism. The term "heme mimetic" refers to an agent that is an analogue of heme and interferes with heme activity, heme synthesis or heme metabolism. Such compound may be produced by a method known in the art or may be obtained commercially.

In certain embodiments, the agent that is an iron mimetic and/or a heme mimetic comprises a non-iron porphyrin.

The term "porphyrin" as used herein refers to a molecule based on a porphyrin structure, and includes derivatives thereof.

In certain embodiments, the non-iron porphyrin comprises a non-iron metalloporphyrin. In certain embodiments, the non-iron porphyrin comprises a non-iron metalloprotoporphyrin.

The term "non-iron metalloporphyrin" refers to an non-iron containing agent having a porphyrin group coordinated to a metal ion (M), as follows:

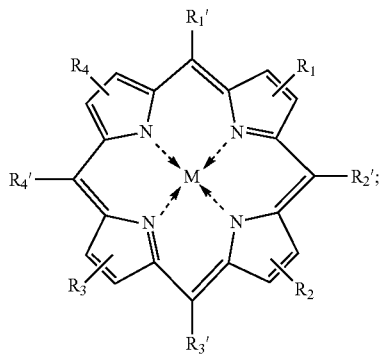

wherein M is a metal ion, and any one or more of R1 to R4 and/or any one or more of R1' t R4' are the same or a different group.

In certain embodiments, the non-iron porphyrin comprises one or more of a gallium protoporphyrin, a manganese protoporphyrin, a zinc protoporphyrin, an indium protoporphyrin, a cobalt protoporphyrin, a ruthenium protoporphyrin, a silver protoporphyrin or a copper protoporphyrin, or any combination thereof.

In certain embodiments, the non-iron porphyrin comprises a gallium protoporphyrin.

In certain embodiments, the non-iron porphyrin comprises a compound with the following structure:

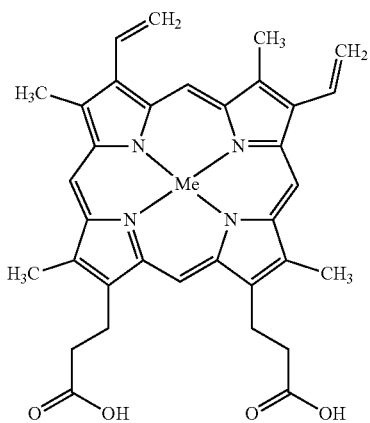

wherein Me is selected from gallium, manganese, zinc, indium, cobalt, ruthenium, silver and copper; and/or an acceptable salt, substituted derivative, solvate, tautomer or stereoisomer thereof. In certain embodiments, Me is gallium.

In certain embodiments, the method comprises exposing the region to a concentration of the agent that is an iron mimetic and/or a heme mimetic as follows: 100 mM or less, 50 mM or less, 20 mM or less, 10 mM or less, 5 mM or less, 4 mM or less, 3 mM or less, 2 mM or less, 1.5 mM or less deferiprone, 1 mM or less, 0.5 mM or less, 0.4 mM or less, 0.3 mM or less, 0.2 mM or less, or 0.1 mM or less.

In certain embodiments, the method comprises exposing the region to a concentration of the agent that is an iron mimetic and/or a heme mimetic as follows: 1 µg/ml or less, 500 µg/ml or less 200 µg/ml or less, 100 µg/ml or less, 50 µg/ml or less, 25 µg/ml or less, 10 µg/ml or less, 5 µg/ml or less, or 1 µg/ml or less.

In certain embodiments, the method comprises exposing the region to 200 µg/ml or less, 100 µg/ml or less, 50 µg/ml or less, 25 µg/ml or less, 10 µg ml or less, 5 µg/ml or less, or 1 µg/ml or less of a non-iron porphyrin.

In certain embodiments, the method comprises exposing the region to 200 µg/ml or less of a non-iron porphyrin.

In certain embodiments, the method comprises exposing the region to a concentration of a non-iron porphyrin in the range from 1 to 200 µg/ml, 5 to 200 µg/ml, 10 to 200 µg/ml, 25 to 200 µg/ml, 50 to 200 µg/ml, 100 to 200 to 100 µg/ml, 5 to 100 µg/ml, 10 to 100 µs/ml, 25 to 100 µg/ml, 50 to 100 µg/ml, 1 to 50 µg/ml, 5 to 50 µg/ml, 10 to 500 µg/ml, 25 to 50 µg/ml, 1 to 25 µg/ml, 5 to 25 µg/ml 10 to 25 µg/ml, 1 to 10 µg/ml, 5 to 10 µg/ml, or 1 to 5 µg/ml.

In certain embodiments, a composition as described herein further comprises an agent that is an iron mimetic and/or a heme mimetic antibiotic.

In certain embodiments, a gel composition as described herein further comprises agent that is an iron mimetic and/or a heme mimetic.

In certain embodiments, the subject is a subject suffering from an existing adhesion. In certain embodiments the method comprises performing an adhesiolytic procedure on the subject to treat the existing adhesion and applying the agent to the region susceptible to formation of a new adhesion.

In certain embodiments, a method as described herein is used to reduce adhesions in a subject by applying a composition comprising the agent to a region susceptible to the formation of an adhesion, to reduce surgical adhesions in a subject by applying a composition comprising the agent to a region susceptible to the formation of an adhesion, to reduce post-operative adhesions in a subject by applying a composition comprising the agent to a region susceptible to the formation of an adhesion, to prevent and/or treat adhesions, and to reduce inflammation associated with adhesions.

In certain embodiments, the present disclosure provides a method of reducing adhesions in a subject, the method comprising applying a composition comprising an agent having iron chelation and/or antioxidant activity to a region susceptible to formation of an adhesion in the subject, thereby reducing adhesions in the subject.

In certain embodiments, the present disclosure provides a method of reducing surgical adhesions in a subject, the method comprising applying a composition comprising an agent having iron chelation and/or antioxidant activity to a region susceptible to formation of a surgical adhesion in the subject, thereby reducing surgical adhesions in the subject.

In certain embodiments, the present disclosure provides a method of reducing postoperative adhesions in a subject, the method comprising applying a composition comprising an agent having iron chelation and/or antioxidant activity to a region susceptible to formation of a postoperative adhesion in the subject, thereby reducing postoperative adhesions in the subject.

In certain embodiments, the present disclosure provides a method of preventing and/or treating a subject for an adhesion, the method comprising applying a composition comprising an agent having iron chelation and/or antioxidant activity to a region susceptible to formation of an adhesion in the subject, thereby preventing and/or treating the subject for an adhesion.

The term "preventing", and related terms such as "prevention" and "prevent", as used herein refers to obtaining a desired therapeutic and/or physiologic effect in terms of arresting or suppressing the appearance of one or more symptoms in the subject.

The term "treatment", and related terms such as "treating" and "treat", as used herein refers to obtaining a desired therapeutic and/or physiologic effect in terms of improving the condition of the subject, ameliorating, arresting, suppressing, relieving and/or slowing the progression of one or more symptoms in the subject, a partial or complete stabilization of the subject, a regression of one or more symptoms, or a cure of the subject.

In certain embodiments, the methods as described herein may be used as part of a therapy to treat existing adhesions, as an adjunct to an adhesiolytic procedure.

In certain embodiments, the present disclosure provides a method of treating a subject for an adhesion, the method comprising:
 (i) performing an adhesiolytic procedure on the subject; and
 (ii) applying a composition comprising an agent having iron chelation and/or antioxidant activity to a region susceptible to formation of an adhesion to reduce formation of a new adhesion in the subject, thereby treating the subject for the adhesion.

It will be appreciated that the application of the composition may occur at one or more of prior to the adhesiolytic procedure, during the adhesiolytic procedure, and after the adhesiolytic procedure.

In certain embodiments, the application of the composition occurs after the adhesiolytic procedure.

In certain embodiments, the present disclosure provides a method of treating a subject for an adhesion, the method comprising:
 (i) performing an adhesiolytic procedure on the subject; and
 (ii) applying a composition comprising an agent having iron chelation and/or antioxidant activity to a region susceptible to formation of an adhesion following the adhesiolytic procedure to reduce formation of a new adhesion in the subject,
 thereby treating the subject for the adhesion.

Certain embodiments of the present disclosure provide use of an agent having iron chelation and/or antioxidant activity.

In certain embodiments, the present disclosure provides use of an agent having iron chelation and/or antioxidant activity- to reduce or prevent and/or treat adhesions in a subject.

Certain embodiments of the present disclosure provide use of an agent having iron chelation and/or antioxidant activity in the preparation of a composition or medicament to prevent and/or treat adhesions in a subject.

Agents having iron chelation and/or antioxidant activity are as described herein. Uses of the agents to reduce adhesions are as described herein.

In certain embodiments, the present disclosure provides use of an agent having iron chelation and/or antioxidant activity in the preparation of a composition or medicament to reduce adhesions in a subject.

In certain embodiments, the present disclosure provides use of an agent having iron chelation and/or antioxidant activity in the preparation of a composition or medicament to prevent and/or treat adhesions in a subject.

Compositions, formulations and medicaments having an agent having iron chelation and/or antioxidant activity are as described herein.

Certain embodiments of the present disclosure provide an agent having iron chelation and/or antioxidant activity for use in reducing adhesions.

Certain embodiments of the present disclosure provide an agent having iron chelation and/or antioxidant activity for use in the treatment of adhesions.

Certain embodiments of the present disclosure provide a composition.

In certain embodiments, the present disclosure provides an anti-adhesion composition comprising an agent having iron chelation and/or antioxidant activity.

Agents having iron chelation and/or antioxidant activity are as described herein.

Methods for assessing the anti-adhesive properties of a composition are as described herein.

Compositions comprising an agent having iron chelation and/or antioxidant activity are as described herein.

In certain embodiments, the anti-adhesion composition comprises one or more of a gel, a solution, a rinse, an emulsion, a cream, nanoparticles, microparticles, and/or liposomes.

In certain embodiments, the composition comprises a gel. In certain embodiments, the composition comprises a hydrogel.

In certain embodiments, the composition comprises a chitosan-based get.

In certain embodiments, the gel comprises one or more of a chitosan, a dextran, a carbohydrate polymer, a hyaluronic acid and/or a salt thereof, a collagen, a carboxymethylcellulose, a gelatine, a polyacylate, and an alginate.

In certain embodiments, the gel comprises a desired release characteristic. Release characteristics of compositions are as described herein.

In certain embodiments, the anti-adhesion composition provides greater than 90% release of the agent within 96 hours. In certain embodiments, the anti-adhesion composition provides greater than 90% release of the agent within 72 hours. In certain embodiments, the anti-adhesion composition provides greater than 90% release of the agent within 48 hours. In certain embodiments, the anti-adhesion composition provides greater than 80% release of the agent within 24 hours.

In certain embodiments, the anti-adhesion composition provides a sustained release of the agent over a period of 3 to 14 days.

In certain embodiments, the agent comprises a reactive oxygen species inhibitor. In certain embodiment, the reactive oxygen species inhibitor comprises a scavenger of reactive oxygen species and/or an inhibitor of generation of reactive oxygen species.

In certain embodiments, the agent comprises one or more of deferiprone, deferoxamine and desferrioxamine, or any combination thereof.

Amounts of the agent in a composition are as described herein.

In certain embodiments, the composition comprises a concentration of deferiprone of 80 mM or less. In certain embodiments, the composition comprises a concentration of deferiprone of 50 mM or less. In certain embodiments, the composition comprises a concentration of deferiprone of 20 mM or less. In certain embodiments, the composition comprises a concentration of deferiprone of 10 mM or less.

In certain embodiments, the anti-adhesion composition further comprises an antibiotic. Examples of antibiotics include aminoglycosides, carhapenems, cephalosporins, glycopeptides, lincoasmides, lipopeptides, macrolides, monobactams, nitrofurans, oxazolidinones penicillins (eg. amoxillicin, amoxicillin and clavunate) peolypeptides, quinolones, fluoroquinones, sulphonamides, and tetracyclines. Antibiotics are commercially available, and methods for their use are known in the art, for example as described in "Therapeutic Guidelines—Antibiotic", Version 15, 2014, published by eTG complete.

Examples of antibiotics include aminoglycosides, carhapenems, cephalosporins, glycopeptides, lincoasmides, lipopeptides, macrolides, monobactams, nitrofurans, oxazolidinones, penicillins, peolypeptides, quinolones, fluoroquinones, sulphonamides, and tetracyclines. Antibiotics are commercially available, and methods for their use are known in the art, for example as described in "Therapeutic Guidelines—Antibiotic", Version 15, 2014, published by eTG complete.

For example, specific antibiotics include one or more of mupirocin, ciprofloxacin ampicillin, amoxycillin, gentamicin, clavulanate, clindamycin, trimethoprim-sulfamethoxazole, doxycycline, minocycline, rifampin, linezolid, flucloxacillin dicloxacillin, cefazolin, cephalothin and cephalexin, clindamycin, lincomycin, erythromycin, rifaximin, levofloxacin, sulbactam, cefoxitin, levofloxacin plus clindamycin or metronidazole, aztreonam, polymyxin E, metronidazole, ampicillin, and amoxicillin, ticarcillin and piperacillin, or in combination with a ß-lactamase inhibitor, such as clavulanic acid, sulbactam, or tazobactam.

In certain embodiments, the antibiotic comprises one or more of mupirocin, gentamicin, doxycycline, metronidazole, amoxicillin, piperacillin, ciprofloxacin, trimethoprim-sulfamethoxazole (Bactrim), or any combination thereof.

In certain embodiments, the anti-adhesive composition is for use for reducing adhesions arising from abdominal surgery and the composition comprises one or more antibiotics as described herein.

In certain embodiments, the anti-adhesive composition is for use for reducing adhesions arising from sinus surgery and the composition comprises one or more antibiotics as described herein.

In certain embodiments, the anti-adhesive composition further comprises an anti-inflammatory agent. Anti-inflammatory agents are as described herein. In certain embodiments, the anti-adhesive composition comprises a corticosteroid, such as budesonide.

In certain embodiments, a composition as described herein further comprises an anti-inflammatory agent, such as a corticosteroid.

In certain embodiments, the present disclosure provides a nasal and/or sinus rinse composition comprising an agent having iron chelation and/or antioxidant activity.

Rinses are as described herein.

In certain embodiments, the present disclosure provides a chitosan based gel comprising an agent having iron chelation and/or antioxidant activity.

Chitosan based gels are known in the art, for example as described in Ahmad et al. (2015) *Res Pharm Sci* 10(1): 1-16.

In certain embodiments, the chitosan based gel further comprises one of more of an iron mimetic, an antibiotic and/or anti-inflammatory agent.

In certain embodiments, the present disclosure provides an anti-adhesion composition comprising a chitosan based gel and an agent having iron chelation and/or antioxidant activity.

Agents having iron chelation and/or antioxidant activity, and their use in gels, are as described herein. Methods for producing chitosan based gels are as described herein.

In certain embodiments, the gel further comprises one or more antibiotics, as described herein. For example, a gel composition may comprise ciprofloxacin at 5 µg/ml.

In certain embodiments, the gel further comprises one or more anti-inflammatory agents, as described herein. For example, a gel composition may comprise budesonide at a concentration of 100 µg/ml.

In certain embodiments, the gel further comprises an agent that is an iron mimetic and/or a heme mimetic. In certain embodiments, the agent that is an iron mimetic or a heme mimetic is present in a composition in an amount ranging from one of the following selected ranges: 1 µg to 1000 mg, 1 µg to 500 mg; 1 µg to 250 mg; 1 µg to 100 mg; 1 µg to 10 mg; 1 µg to 1 µg; 1 µg to 100 µg; 1 µg to 10 kg; 10 µg to 1000 mg; 10 µg to 500 mg; 10 µg to 250 mg, 10 µg to 10 mg; 10 µg to 1 mg; 10 µg to 100 µg; 100 µg to 1000 mg, 100 µg to 500 mg, 100 µg to 250 mg, 100 µg to 100 mg; 100 µg to 10 mg; 100 µg to 1 mg; 1 mg to 1000 mg, 1 mg to 500 mg, 1 mg to 250 mg, 1 mg to 100 mg; 1 mg to 10 mg, 10 mg to 1000 mg, 10 mg to 500 mg, 10 mg to 250 mg, 10 mg to 100 mg, 100 mg to 1000 mg, 100 mg to 500 mg, 100 mg to 250 mg and 500 mg to 1000 mg. Other amounts are contemplated.

In certain embodiments, the present disclosure provides an anti-adhesive composition comprising an agent having iron chelation and/or antioxidant activity and one or more of an antibiotic, anti-inflammatory agent and an iron mimetic.

For example, the composition may be a chitosan based gel comprising an agent having iron chelation and/or antioxidant activity (eg deferiprone) and one or more of an antibiotic (eg ciprofloxacine), an anti-inflammatory agent (eg budesonide) and an iron mimetic (eg gallium protoporphyrin), or any combination thereof.

Certain embodiments of the present disclosure provide a method of reducing adhesions using a composition as described herein.

In certain embodiments, the present disclosure provides a method of reducing adhesions in a subject, the method comprising applying a composition as described herein to a region susceptible to formation of an adhesion in the subject, thereby reducing adhesions in the subject.

In certain embodiments, the adhesions comprise postoperative sinus adhesions.

In certain embodiments, the present disclosure provides a method of reducing postoperative sinus adhesions in a subject, the method comprising using a nasal and/or sinus rinse composition as described herein to rinse the sinuses in the subject and thereby reducing postoperative sinus adhesions in the subject.

Certain embodiments of the present disclosure provide a method of reducing inflammation using a composition as described herein.

Certain embodiments of the present disclosure provide a kit or product.

In certain embodiments, the kit or product comprises: (i) an agent having iron chelation and/or antioxidant activity; and/or (ii) one or more components for forming a composition; and/or (iii) one or more other reagents as described herein; and/or (iv) instructions for performing a method as described herein.

Certain embodiments of the present disclosure provide a kit or product for performing a method as described herein.

Certain embodiments of the present disclosure provide products for reducing for reducing adhesions, or for preventing and/or treating adhesions.

In certain embodiments, the present disclosure provides a product for reducing adhesions in a subject, the product comprising the following components:
  (i) an agent having iron chelation and/or antioxidant activity; and/or
  (ii) one or more components for forming a gel comprising an agent having iron chelation and/or antioxidant activity, the gel being suitable for application to a surgical site; and/or
  (iii) a pre-formed gel comprising an agent having iron chelation and/or antioxidant activity, wherein the gel is suitable for application to a surgical site;
  and optionally
  (a) an applicator for dispensing gel comprising the agent to a surgical site; and/or
  (b) instructions for forming the gel and/or dispensing the gel to a surgical site.

Agents having iron chelation and/or antioxidant activity are as described herein.

In certain embodiments, the agent comprises one or more of deferiprone, deferoxamine and desferrioxamine, or any combination thereof.

The agent may be supplied in a suitable form. In certain embodiments, the agent may be supplied in solid or lyophilised form, and may be optionally admixed with one or more other reagents.

In certain embodiments, the agent may be supplied in liquid form, and may be optionally combined with one or more other reagents, such as stabilising agents.

For example, the agent having iron chelation and/or antioxidant activity may be in a form suitable for introduction into one or more other components used to form a gel.

In certain embodiments, the one or more components for forming a gel comprise the following:
  (i) one or more base solutions, and optionally one or more of which may also comprise the agent having chelation and/or antioxidant activity; and
  (ii) a gelling agent or gelling solution for combining with the base solution(s) to form a gel.

For example, for the formation of a chitosan dextran gel, the product may contain a solution of deferiprone (which is provided at a suitable concentration that when a gel is formed is at the desired final concentration), a solution of chitosan and a solution of dextran.

An example of a pre-formed gel is a chitosan-dextran gel containing deferiprone at a suitable concentration. Other types of gels are as described herein.

In certain embodiments, the applicator is a syringe. Other types of applicators are contemplated.

The product may further contain one or more other components, for example one or more other components for assisting with dispensing of the gel, such as a dispensing tip for a syringe, and/or one or more dyes for visualizing a region or site for application of the gel.

In certain embodiments the product is a nasal and/or a sinus rinse.

In certain embodiments, the present disclosure provides a nasal and/or a sinus rinse solution, the solution comprising an agent having iron chelation and/or antioxidant activity and a liquid carrier.

In certain embodiments, the present disclosure provides a nasal and/or a sinus rinse solution, the solution comprising an agent having iron chelation and/or antioxidant activity and a saline solution.

In certain embodiments, the present disclosure provides a product for reducing post-operative sinus adhesions in a subject, the product comprising the following components:
  (i) a solution comprising an agent having iron chelation and/or antioxidant activity (typically containing around 1-2% saline);
  and optionally
  (a) an applicator for delivering the solution to the nasal and/or sinus passages; and/or
  (b) instructions for delivering the solution using the applicator.

Certain embodiments of the present disclosure provide a method for producing anti-adhesive products. Methods for producing anti-adhesive products are as described herein.

In certain embodiments, the anti-adhesive product comprises a gel. In certain embodiments, the anti-adhesive product comprises a solution or rinse.

In certain embodiments, the present disclosure provides a method of producing a product for reducing adhesions in a subject, the method comprising forming a gel comprising an agent having iron chelation and/or antioxidant activity, wherein the gel is suitable for application to a region or site susceptible to the formation of an adhesion.

Methods for forming gels are as described herein.

Regions or sites susceptible to the formation of an adhesion are as described herein. In certain embodiments, the region is a surgical site.

Certain embodiments of the present disclosure provide a method of screening or identifying agents for reducing adhesions, or screening or identifying agents for preventing and/or treating adhesions.

In certain embodiments, the present disclosure provides a method of identifying an agent for reducing adhesions, the method comprising determining the ability of an agent having iron chelation and/or antioxidant activity to reduce adhesions in a subject, thereby identifying the agent as an agent for reducing adhesions.

In certain embodiments, the present disclosure provides a method of identifying an agent for preventing and/or treating adhesions, the method comprising determining the ability of an agent having iron chelation and/or antioxidant activity to reduce adhesions in a subject, and thereby identifying the agent as an agent for preventing and/or treating adhesions.

Methods for determining the ability of an agent to reduce adhesions, or to prevent or treat adhesions, are as described herein.

In certain embodiments, the method comprises use of an animal model.

In certain embodiments, the method comprises determining the ability of an iron chelator to reduce adhesions in a subject. In certain embodiments, the method comprises determining the ability of an antioxidant agent to reduce adhesions in a subject. In certain embodiments, the method comprises determining the ability of an agent having both iron chelation activity and antioxidant activity to reduce adhesions in a subject.

Certain embodiments of the present disclosure provide an anti-adhesive agent identified using the screening methods described herein.

Certain embodiments of the present disclosure provide a method of inhibiting proliferation and/or migration of fibroblasts by exposing the fibroblasts to an agent having iron chelation and/or antioxidant activity, as described herein.

In certain embodiments, the present disclosure provides a method of inhibiting proliferation and/or migration of fibroblasts, the method comprising exposing the fibroblasts to an agent having iron chelation and/or antioxidant activity, thereby inhibiting proliferation and/or migration of the fibroblasts.

Agents having iron chelation and/or antioxidant activity are described herein. In certain embodiments, the agent comprises a reactive oxygen species inhibitor. In certain embodiments, the reactive oxygen specifies inhibitor comprises a scavenger of reactive oxygen species and/or an inhibitor of generation of reactive oxygen species. In certain embodiments, the agent comprises one or more of deferiprone, deferoxamine and desferrioxamine.

Methods for exposing fibroblasts to an agent are as described herein.

In certain embodiments, the method comprises exposing the fibroblasts to a concentration of deferiprone of 80 mM or less. In certain embodiments, the method comprises exposing the fibroblasts to a concentration of deferiprone of 50 mM or less. In certain embodiments, the method comprises exposing the fibroblasts to a concentration of deferiprone of 20 mM or less. In certain embodiments, the method comprises exposing the fibroblasts to a concentration of deferiprone of 10 mM or less.

In certain embodiments, the method comprises inhibiting proliferation of the fibroblasts by at least 30% within 48 hours of exposure of the fibroblasts to the agent. In certain embodiments, the method comprises inhibiting proliferation of the fibroblasts by at least 50% within 72 hours of exposure of the fibroblasts to the agent.

In certain embodiments, the exposing of the fibroblasts to the agent comprises exposing the fibroblasts to a composition comprising the agent.

Compositions comprising an agent having iron chelation and/or antioxidant activity are described herein.

In certain embodiments, the composition comprises one or more of a gel, a solution, a rinse, an emulsion, a cream, nanoparticles, microparticles, and/or liposomes.

In certain embodiments, the composition comprises a gel. In certain embodiments, the composition comprises a hydrogel. Gels are as described herein.

In certain embodiments, the gel comprises one or more of a chitosan, a dextran, a carbohydrate polymer, a hyaluronic acid and/or a salt thereof, a collagen, a carboxymethylcellulose, a gelatine, a polyacylate, and an alginate. Other agents for use in forming a gel are contemplated.

In certain embodiments, the composition provides greater than 90% release of the agent within 96 hours. In certain embodiments, the composition provides greater than 90% release of the agent within 72 hours. In certain embodiments, the composition provides greater than 90% release of the agent within 48 hours. In certain embodiments, the composition provides greater than 80% release of the agent within 24 hours.

In certain embodiments, the composition comprises a desired release characteristic. Release characteristics of compositions are as described herein.

In certain embodiments, the composition provides a sustained release of the agent over a period of 3 to 14 days.

In certain embodiments, the fibroblasts are human fibroblasts. In certain embodiments, the fibroblasts are animal fibroblasts.

In certain embodiments, the fibroblasts are in vitro. For example, the cells may be cultured fibroblasts.

In certain embodiments, the fibroblasts are in vivo. Methods for exposing fibroblasts in vivo to an agent having iron chelation and/or antioxidant activity are described herein.

In certain embodiments, the fibroblast proliferation and/or migration is associated with the formation of an adhesion in a subject.

In certain embodiments, the fibroblasts comprise fibroblasts at, near, or in the vicinity of a surgical site.

Certain embodiments of the present disclosure provide methods for screening or identifying inhibitors of fibroblast proliferation and/or migration.

In certain embodiments, the present disclosure provides a method of identifying an inhibitor of fibroblast proliferation and/or migration, the method comprising determining the ability of an agent having iron chelation and/or antioxidant activity to inhibit proliferation and/or migration of fibroblast, and thereby identifying the agent as an inhibitor of fibroblast proliferation and/or migration.

Certain embodiments of the present disclosure provide an anti-fibroblastic agent identified using the screening methods described herein.

The present disclosure is further described by the following examples. It is to be understood that the following description is for the purpose of describing particular embodiments only and is not intended to be limiting with respect to the above description.

Example 1—Deferiprone Inhibits Proliferation of Fibroblasts

We first chose to investigate the effect and timing of the antioxidant and iron chelator deferiprone on fibroblast proliferation using an in vitro proliferation assay.

1, Materials and Methods

Alamar Blue Proliferation Assay

Fibroblasts were seeded at a density of $2 \times 10^4$ cells/well in 96 well plates (Nuns, Sydney Australia) and cultured at 37° C., 5% $CO_2$ for 24 hours Media was aspirated and cells were washed twice in phosphate buffered saline. The following treatments were used:

(i) No treatment control (NTC)—DMEM (Invitrogen, Sydney Australia) containing Penicillin at 500 U/mL, Streptomycin and Amphotericin B (Sigma-Aldrich, MO) at 0.5 mg/mL, 10% Fetal Bovine Serum.
(ii) 5 mM of Deferiprone dissolved in control media.
(iii) 10 mM Deferiprone dissolved in control media.
(iv) 20 mM Deferiprone dissolved in control media.

Readings were taken at 4, 24, 48 and 72 hours. At each time point media was aspirated and fresh control media with 10% Alamar Blue was added and incubated in the dark for 6 hours at 37° C. 5% $CO_2$. The plate was then read at 570 and 595 nm according to manufacturer's instructions.

2. Results

Anti-Proliferative Effects

Fibroblasts proliferation was measured using the Alamar Blue reduction assay. The assay is based on use of resazurin, a non-toxic, cell permeable compound which is blue in colour and non-fluorescent. Resazurin is reduced to resorufin a compound that is red in colour and highly fluorescent. Viable cells continuously convert resazurin to resorufin, increasing the overall fluorescence and colour of the media surrounding cells.

The results are shown in FIG. 1. The data shows that there is a significant dose dependent effect of deferiprone in inhibiting fibroblast proliferation, as measured by 2-way analysis of variance (ANOVA).

In addition, it was found that the inhibition of proliferation was time dependent, and occurred over a period of at least 24 to 72 hours.

Previous studies have demonstrated that the critical time interval to block adhesion formation is primarily in the first 48 hours after initial injury, and the extent of adhesion formation is dependent on the inhibition of fibroblast proliferation and migration during that time.

Deferiprone inhibits proliferation of fibroblasts at least in the time period measured of 24 to 72 hours, which coincides with the critical time interval to block adhesion formation.

Example 2—Dose and Time-Dependent Effect of Deferiprone on Primary Fibroblast Cell Migration A fibroblast wound healing protocol was used to investigate the effect of deferipone on fibroblast migration.

1. Fibroblast Wound Healing Protocol

Fibroblasts were stained with CellTrace Proliferation Kit (Thermo-Fisher Scientific, Life Technologies, CA) and prepared in a suspension of $3 \times 10^5$ cells/mL of DMEM (Invitrogen, Sydney Australia) containing Penicillin at 500 U/mL, Streptomycin and Amphotericin B (Sigma-Aldrich, MO) at 0.5 mg/mL, 10% Fetal Bovine Serum. 70 uL of this suspension were seeded into each chamber inserts of the Ibidi culture-insert 24 (Ibidi GmbH, Munich, Germany) and cultured for 12 hours at 37° C., 5% $CO_2$. The inserts were then removed with sterile forceps and cells washed twice in phosphate buffered saline.

The following treatments were used:
(i) No treatment control (NTC) DMEM (Invitrogen, Sydney Australia) containing Penicillin at 500 U/mL, Streptomycin and Amphotericin B (Sigma-Aldrich, MO) at 0.5 mg/mL 10% Fetal Bovine Serum.
(ii) 5 mM of Deferiprone dissolved in control media.
(iii) 10 mM Deferiprone dissolved in control media.
(iv) 20 mM Deferiprone dissolved in control media.

The effects on cells were recorded in real time at 37° C., 5% $CO_2$ and imaged at intervals of 0, 8, 24 and 48 hours using Zeiss LSM700 Confocal (Carl Zeiss, Oberkochen, Germany) until gap closure. Image properties: DAPI blue signal; 405 nm laser; line step 2; line average 4; bit 12; zoom 0.5; 512×512 pixels; time series.

Figure 2:
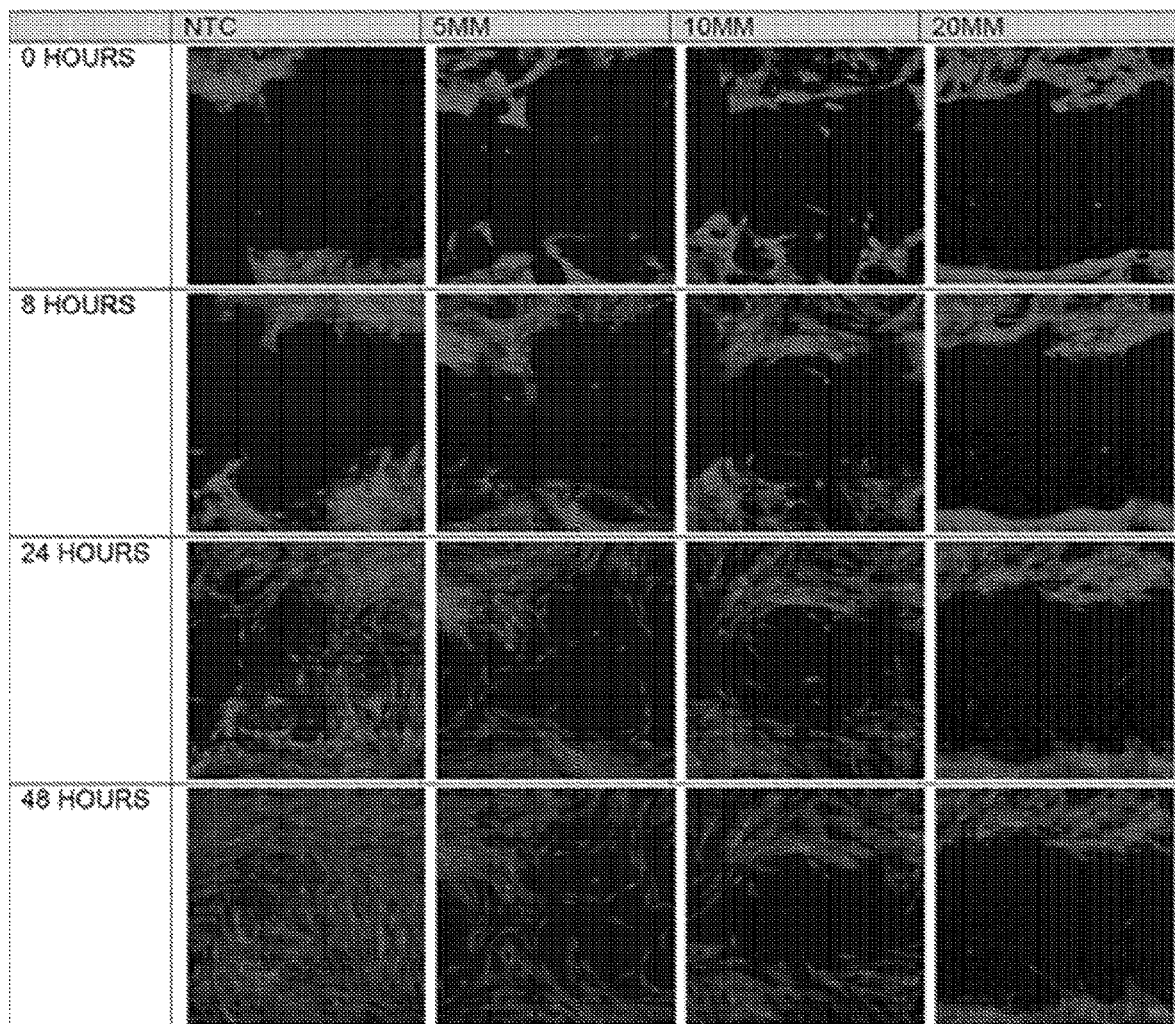
FIG. 2 shows dose and time-dependent effect of Def on primary fibroblast cell proliferation over 48-72 hours. Primary fibroblasts were stained with CytoX-Violet migrate and close a void in fibroblasts after 48 hours in control cells (first column, 0 mM Def) as compared to minimal closure in 20 mM Def treated fibroblasts for up to 48 hours (last column, 20 nM Def).

The results are shown in FIG. 2, which shows a dose and time-dependent effect of deferiprone on primary fibroblast cell proliferation over 48 to 72 hours. Primary fibroblasts migrate and close a void in fibroblasts after 48 hours in control cells (first column, 0 mM deferiprone) as compared to minimal closure in 20 mM deferiprone treated fibroblasts for up to 48 hours (last column, 20 mM deferiprone).

As such, we also found that deferiprone inhibited fibroblast migration within 48 hours, which coincides with the critical time interval to block adhesion formation in vivo.

Example 3—Gel Formulation and Release Characteristics

A hydrogel formulation was prepared as described in WO/2009028965 and Paramasivan S, Jones D, Baker L, Hanton L, Robinson S, Wormald P J, Tan L, Am Rhinol Allergy 2014, 28, 361, and loaded with 20 mM of deferiprone (3-hydroxy-1,2-dimethylpyridin-4(1H)-one, Sigma Aldrich, Steinheim, Germany).

Drug release: Five millilitres of gel containing deferiprone was prepared in a Falcon tube and allowed to solidify, after which 10 ml of release medium (phosphate buffered saline, Sigma. Aldrich) was added. The tube was incubated at 37° C. on a rotating platform for 20 days. Aliquots of 0.5 ml were taken at specific time points (0.5, 1, 2, 8, 16, 24, 48, 72, 96, 120, 170, 220, 290, 460 hours) and replaced with fresh release medium. The concentration of deferiprone was quantified by UV-Vis spectroscopy (Evolution 201 UV-Vis Spectrophotometer, Thermo Fisher Scientific, Scoresby, VIC, Australia) at 280 nm and 405 nm, respectively, by interpolating from a standard curve.

Figure 3:
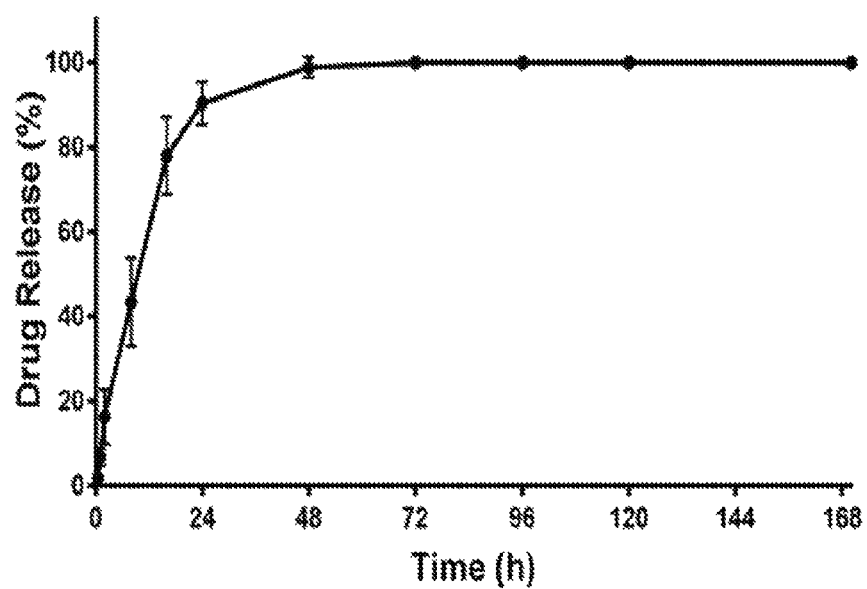
FIG. 3 shows the release profile of a gel loaded with 20 mM deferiprone (Def). Data are the mean±SD of 3 replicates.

The data is shown in FIG. 3, The concentration of deferiprone in the release medium was expressed as a percentage of the original concentration in the gel.

Deferiprone is effectively released from the gel over 48 hours. The gel provides a vehicle for the immediate and complete release of deferipone, with the maximum release occurring after 48 hours (FIG. 3). The release of deferiprone reached 100% after approximately 48-72 hours.

As such, the hydrogel formulation provides a drug-delivery-system which facilitates a release of deferiprone coinciding with the critical time interval to block adhesion formation in vivo.

A suitable hydrogel for adhesions is 1% succinyl-chitosan, 3% dextram aldehyde in 0.24% sodium phosphate buffer pH 7.4, and containing a suitable concentration of agent.

Example 4—Deferiprone Embedded in a Hydrogel Reduce Post-Laminectomy Adhesions in a Sheep Model A post-laminectomy model was used as a model for investigating formation of adhesions in animals.

Post-laminectomy adhesions are considered to be a significant cause of post-operative back pain. One possible mechanism behind this is believed to include the presence of a post-operative haematoma with subsequent fibroblast migration into this region. Fibroblasts then cause adhesions to form with traction on sensory nerves in this region.

In this study we sought to determine the effect of a hydrogel combined with deferiprone in reducing the incidence and severity of post-laminectomy adhesions.

Methodology:

Six (6) merino sheep were given general anaesthetic using intravenous ketamine and diazepam for induction and isoflurane for maintenance and placed prone with pressure points adequately protected on a bean bag using previously described methodology (Rajiv et al. (2013) *Acta Neurochirurgica* 155(7):1361-6) to prevent compartment syndrome. A 20 cm long midline posterior incision was made on each sheep and a sub-periosteal midline dissection made to the lamina. The spinous processes were removed at 3 levels and the lamina removed with combination high-speed drill and rongeurs. The dura was exposed and 2 ml kaolin mixed with normal saline placed on the intact dura. Kaolin is known to induce adhesions following topical administration and has been used intradurally (Wong et al (2012) *Neurosurgery.* 71(2):474-80).

Following kaolin application, each site was randomized to receive nothing (control), gel with deferiprone (20 mM), or gel with a corticosteroid (budesonide, 100 μg/ml). The hydrogel is as described in Example 3.

The wound was then closed in a layered fashion to eliminate surgical dead-space with dissolving vicryl sutures. Animals were recovered. Antibiotics and systemic non-steroidal anti-inflammatories were given for 5 days post operatively. The animals were returned to a paddock for 3 months where free roaming was possible. At the end of three months, animals underwent MRI of the spine. Sagittal and transverse spin echo T1 and fast spin echo T2 of the whole spine was performed. The spine sequences were T1 Sagittal (TR/TE 503/11; Thickness 3 mm), T2 Sagittal (TR/TE 2830/102; Thickness 3 mm), STIR Sagittal (TR/TE 4840/63; Thickness 3 mm), T2 GRE Sagittal (TR/TE 750/26; Thickness 3 mm) and T2 Axial (TR/TE 6970/118; Thickness 4 mm).

Fibrosis was scored by assessing the hypo-intense area in the epidural region utilizing the scoring system used by Rajiv et al. (2013) *Acta Neurochirurgica* 155(7):1361-6. Each level was divided into 15 slices. Grade 1—No abnormalities, Grade 2—abnormalities on <8 slices. Grade 3—Abnormalities on >8 slices but less than 1 mm thick, Grade 4 Abnormalities on >8 slices and >1 min thick.

Following MRI, the sheep underwent humane killing. The ventral and dorsal musculature was removed and the hone anterior to the spinal dura and cord was removed with high speed drill and rongeurs. The thecal sac was then pulled anteriorly by a surgeon blinded to treatment condition. The resistance to removal encountered was graded using the scoring system described by Richards et al (2010) *Journal of Biomedical Materials Research Part B—Applied Biomaterials*. 9213:439-46. Grade 0—no adhesions; Grade 1—thin membranous threads, easily detachable; Grade 2—slight adhesion, requiring only minimal blunt dissection; Grade 3—moderate adhesions requiring some sharp dissection; and Grade 4—severe adhesions requiring extensive sharp dissection. The specimen was then fixed in formalin and section and stained for histological examination. The histology grading system used by Richards et al was used to grade the adhesions (Richards et al (2010). *Journal of Biomedical Materials Research Part B—Applied Biomaterials*. 92B:439-46). Grade 0—no adhesions, Grade 1—<25% affected; Grade 2—25-50% affected; Grade 3 >50% but <100% affected and Grade 4—dense 100% adhesion.

Specimens were formalin fixed and embedded in paraffin blocks. Hematoxylin and Eosin stains were performed.

Post-operative recovery and clinical examinations of the sheep were uneventful for all sheep over a 3-month period following surgery. MRI and histopathology showed absent toxicity and significantly reduced adhesion scores of paraspinal muscle fibres to the dura at three months post operatively in the deferiprone gel treated sheep.

In the control specimens, dense adhesions were seen with muscle fibres attached to the dural surface. There were also significant amounts of refractile foreign material seen with an acute, florid polymorphonuclear reaction with macrophage infiltration. There were large numbers of fibroblasts seen infiltrating the dura.

In the corticosteroid group, the adhesions were less florid however they were still significant. Large numbers of fibroblasts were seen infiltrating the dura. There was a significant polymorphonuclear reaction.

In the deferiprone group, there was a marked decrease in fibroblast migration into the dura compared with the other two groups with less inflammation and adhesion seen. The dural layers remained organized.

Figure 4:
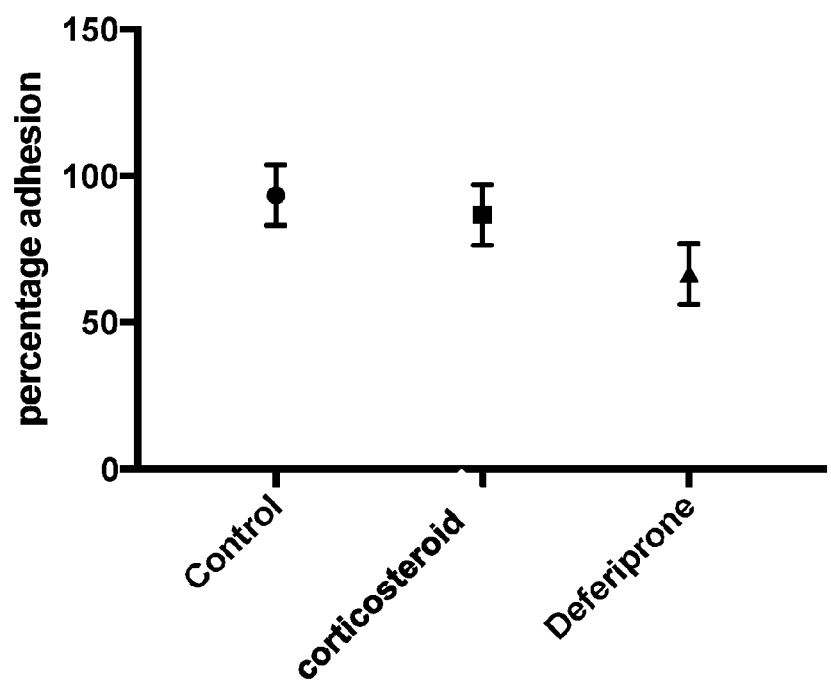
FIG. 4 shows that deferiprone gel is effective in reducing adhesion formation post spinal surgery in vivo as compared to no treatment control or gel containing corticosteroid.

The results are quantified in FIG. 4. Deferiprone-gel was found to be safe and effective in reducing adhesion formation post spinal surgery in vivo without affecting bone or dura healing.

The results showed severe adhesions for the control surgical sites, and a significant reduction in adhesions for the deferiprone-gel treated sites (mean adhesion scores of 93.33%+/−10.33 for the no-treatment control treated surgical sites compared to 86.67%+/−10.33 for corticosteroid-gel compared to 66.67%+/−10.33 for the deferiprone-gel treated sites, P=0.0076, Kruskal-Wallis). No differences were observed in bone or dura healing in any of the sheep.

Together, these results demonstrate the potent anti-adhesive properties of the deferiprone-gel (with absent toxicity) in vivo.

Example 5 Medical Products for Reduction of Adhesions

Agents having iron chelation and/or antioxidant activity may be used in medical products for reducing the formation of adhesions.

Examples of medical products using a gel formulation with the agent are described below.

1. Product for Spinal Surgery

The gel is intended to be placed at sites of tissue following surgical procedures such as laminectomy, laminotomy, and/or discectomy.

A product may contain one or more components for forming a gel with an agent having iron chelation and/or an antioxidant activity, and/or may contain pre-formed gel with the agent. The components for forming the gel, or the pre-formed gel, will typically be supplied sterile and for single use only.

In the case where a pre-formed gel is used, the gel may be pre-loaded into a syringe for dispensing to the surgical site.

For gel to be formed immediately prior to application, solid dextran aldehyde may be mixed with a solution of succinyl-chitosan and a solution of buffer containing the agent (eg deferiprone) to produce a 1% succinyl-chitosan, 3% dextram aldehyde in 0.24% sodium phosphate buffer pH 7.4.

The gel formed may then be taken up into a syringe.

Prior to dispensing, the cap on the syringe is removed and an applicator tip may be secured to the syringe to assist with dispensing.

Following the primary surgical procedure, and immediately prior to closing the incision, the gel may be applied to coat the dura and exiting nerve root along both its dorsal and ventral surfaces. The gel will typically be applied to the site of the laminectomy/laminotomy to fill depth of the surgical site to the level of the ventral surface of the vertebral lamina. The surgical procedure is then concluded according to standard technical practice.

A product/kit supplied may have the following contents:
(a) Syringe 3 to 5 mL Otter lock) may be pre-loaded with gel containing agent.
(b) Applicator tip (leer lock)
(c) Pre-formed gel containing agent, and/or separate components for forming gel (eg chitosan solution, dextran aldehyde solid/solution, buffer and stock solution of agent)
(d) instructions for use, including product tracking labels 2. Product for Tendon Surgery A gel containing an agent having iron chelation and/or antioxidant may be used for the prevention of adhesions as a result of tendon and/or peripheral nerve surgery, such as shoulder and hand surgery.

For gel to be formed immediately prior to application, solid dextran aldehyde may be mixed with a solution of succinyl-chitosan and a solution of buffer containing the agent (eg deferiprone) to produce a 1% succinyl-chitosan, 3% dextram aldehyde in 0.24% sodium phosphate buffer pH 7.4.

The gels may also be pre-formed

Typically, the gel will be made from sterile components or provided in sterilized form.

The gel is intended to be placed around tendon and peripheral nerve tissues by the surgeon to reduce adhesion formation.

For pre-formed gel supplied pre-loaded in a syringe, the syringe cap is to be removed and an applicator tip secured to the syringe.

For gel to be formed immediately prior to application, the gel formed may then be taken up into a syringe and an applicator tip secured to the syringe.

Following tendon and peripheral nerve repair, and prior to closure of the access site incision, the gel may be applied between tendon and sheath and along the surface of the tendons and nerves and surrounding tissues, by covering the tissue surfaces with the gel.

A product/kit supplied may have the following contents:
(a) Syringe 3 to 5 mL (Luer lock) may be pre-loaded with gel containing agent.
(b) Applicator tip (luer lock)
(c) Pre-formed gel containing agent, and/or separate components for forming gel (eg chitosan solution, dextran aldehyde solid/solution, buffer and stock solution of agent)
(d) Instructions for use, including product tracking labels.

3. A Sinonasal Rinse for Use after Sinus Surgery

A solution for rinsing the sinuses after surgery may be used to reduce the formation of adhesions, by applying a solution to the nasal and sinuses. Deferiprone also has anti-inflammatory properties, particularly on human nasal epithelial cells and human sinonasal fibroblasts, which assists with the use of the rinse for treatment after sinus surgery.

A product/kit supplied may have the following contents:
(a) solid iron-chelating agent and/or an anti-oxidant agent for dissolution; and/or
(b) pre-formed solution for rinsing containing an iron-chelating agent and/or an anti-oxidant agent (typically containing 1 to 2% salt and optionally a buffer);
and optionally
(c) a squeeze bottle or a syringe; and/or
(d) instructions for use.

Example 6—Screening for Therapeutic Agents for Reducing Adhesions

One embodiment of a screening assay for investigating the ability of a candidate agent to reduce adhesions is as follows:
(i) The ability of a candidate agent to inhibit fibroblast proliferation and/or migration may be investigated as described in Examples 1 and 2.
(ii) For a candidate agent found to have the ability to inhibit fibroblast proliferation and/or migration, a composition containing the candidate agent, such as a gel composition containing the agent, may be produced for testing in an animal model of adhesion, for example as described in Example 4.
(iii) Candidate agents that have the ability to inhibit adhesions in an animal model are possible therapeutic agents for reducing adhesions. Such agents may be subjected to further safety and efficacy trials.

It will be appreciated that the step of testing the ability of a candidate agent to inhibit fibroblast proliferation and/or migration may be employed as a pre-screening step, and that candidate agents may be tested directly in an animal model.

Example 7—Effect of Deferiprone on Human Primary Nasal Fibroblasts and Human Primary Nasal Epithelial Cells 1. Methods Study Population The study was approved by the Queen Elizabeth Hospital Human Ethics Committee, and written informed consent was obtained from all participants for tissue collection and use of clinical information. Patients recruited to the study included those who were undergoing endoscopic sinus surgery for CRS. Exclusion criteria included active smoking, age less than 18 years, pregnancy, and systemic diseases (immunosuppressive disease).

Harvesting and culturing primary Human Nasal Fibroblasts in Vitro.

Sinonasal tissue was biopsied from paranasal sinus mucosa and transferred to a 6-well culture plate with 2 ml Dulbecco's Modified Eagle's medium (DMEM, Invitrogen, UK) supplemented with 1:100 L-glutamine, 10% Fetal bovine serum (FBS, Sigma-Aldrich), 1:100 ascorbic acid 2-phosphate, and 1:100 penicillin streptomycin (Gibco, Life Technologies) and incubated. Every 2-3 days, the tissue was washed gently with 1 ml phosphate-buffered saline (PBS) and medium was replaced with 1.5 ml fresh medium until fibroblasts became confluent after approximately 2 weeks.

Purification of Fibroblasts

Once confluent, fibroblasts were washed with 2 ml PBS, trypsinized and collected followed by centrifugation at 400×g for 8 minutes. The supernatant was removed and pellet resuspended in 1 ml PBS along with 50 µl Dynabeads Epithelial Enrich (Invitrogen, USA). The tube was wrapped in parafilm and placed on a rotor mixer for 20 minutes at room temperature (RT). Supernatant containing fibroblasts were transferred to a T25 tissue culture flask and the tube containing the remaining beads discarded Harvesting and Culturing Human Nasal Epithelial Cells in Vitro Primary human nasal epithelial cells (HNECs) were harvested from nasal polyps by gentle brushing in a method described by Ramezanpour et al. (2016) "Th17 cytokines disrupt the airway mucosal barrier in chronic rhinosinusitis" Mediators of inflammation; 2016: 9798206. doi: 10.1155/2016/9798206. Extracted cells were suspended in Bronchial Epithelial Growth Media (BEGM, CC-3170, Lonza, Walkersville, Md., USA), supplemented with 2% Ultroser G (Pall Corporation, Port Washington, N.Y., USA). The cell suspension was depleted of macrophages using anti-CD68 (Dako, Glostrup, Denmark) coated culture dishes, and HNECs were maintained with B-ALI™ growth medium (Lonza, Walkersville, USA) in collagen coated flasks (Thermo Scientific, Walthman, Mass., USA) in a cell incubator at 37° C. with 5% $CO_2$.

Air Liquid Interface Culture

HNECs were grown until 80% confluent then harvested for seeding onto collagen coated 6.5 mm permeable Transwell plates (BD Biosciences, San Jose, Calif., USA) at a density of $5 \times 10^4$ cells per well. Cells were maintained with B-ALI™ growth medium for 2-3 days in a cell incubator at 37° C. with 5% $CO_2$. On day 3 after seeding, the apical media was removed and the basal media replaced with B-ALI™ differentiation media, exposing the apical cell surface to the atmosphere. Human nasal epithelial cultures at air liquid interface (HNEC-ALI) were maintained for a minimum of 14 days for development of tight junctions and 28 days for cilia generation.

Cytotoxicity Studies

Primary human fibroblasts or epithelial cells were grown in DMEM and BEGEM (Lonza, Walkersville, USA) medium respectively. Cells were maintained in a fully humidified incubator with 5% $CO_2$ at 37° C. prior to cytotoxicity studies. Cells were exposed to different concentrations of Deferiprone (3-Hydroxy-1,2-dimethyl-4(1H)-pyridone, Sigma, USA) at different time points, followed by determination of lactate dehydrogenase (LDH) with a cytotoxicity detection kit (Promega, Madison, U.S.), Briefly, 50 μL of the supernatant from each well was mixed with 50 μL of LDH reagent and was incubated for 30 minutes in the dark at RT. The optical density (OD) was measured at 490 Mil on a FLUOstar OPTIMA plate reader (BMG Labtech, Ortenberg, Germany), Cell culture studies were performed as three independent experiments.

Wound Healing (Migration) Assay

In the fibroblast wound closure assay, fibroblasts were seeded in 24 well plates, stained with CellTrace™ Violet (Invitrogen/Life Technologies, USA) and allowed to get 80% confluent in 24 hours. A straight vertical scratch was made down through the fibroblast and HNEC-ALI cell monolayers by using a 200 μl pipette tip. The media and cell debris was aspirated carefully and culture media with different concentrations of deferiprone (1 mM, 5 mM, 10 mM, 20 mM) or media only (negative control) added to each well for 72 hours. At time zero, cells were treated with 1 μg/ml mitomycin (Accord Healthcare Inc, NDC 16729-108-11, USA) to inhibit cell proliferation. The wound closure (cell migration) was recorded using time-lapse LSM700 confocal scanning laser microscopy (Zeiss Microscopy, Germany), with an image recorded every 4 hours in a temperature and $CO_2$ controlled chamber. Data was analysed using Image.

Proliferation Assay

Fibroblasts were established at $0.5 \times 10^6$ cells/ml in a 24 well plate and incubated overnight to allow adherence. The cells were treated with different concentrations of deferiprone (1 mM, 5 mM, 10 mM, 20 mM) for 48 h at 37° C. in 5% CO2. Cells were harvested by trypsinisation then fixed with 3 ml ice-cold 70% ethanol at −20° C. overnight. The cell pellet was resuspended in 1 ml of mixture solution (20 μg/ml of propidium iodide (PI) and 200 μg/ml of RNase (R-5503, Sigma, USA) in 0.1% Triton X-100 in phosphate buffered saline (PBS) and incubated at RT in the dark for 30 mins. Samples were analysed using a BD FACSCanto™ II flow cytometer.

Enzyme-Linked Immunosorbent Assay (ELISA)

Supernatants were collected from HNECs and fibroblasts after 24 hours of exposure with different concentrations of deferiprone in the presence/absence of the pro-inflammatory agent Poly (I:C) (10 μg/ml) or IL-1β (10 ng/ml Sigma, Saint Louis, USA) respectively. Interleukin-6 (IL-6) protein levels were estimated with an ELISA kit using rat anti-human IL-6 antibodies (BD Biosciences, New Jersey, USA), according to the manufacturer's instructions. All measurements were performed in duplicate using a FLUOstar OPTIMA plate reader (BMG Labtech, Ortenberg, Germany). The tissue sample concentration was calculated from a standard curve and corrected for protein concentration.

Collagen Assay

Primary human nasal fibroblasts were seeded in 24-well tissue-culture plates at a density of $5 \times 10^5$ grown in DMEM until confluent. Duplicate wells were stimulated with deferiprone at 1 mM, 5 mM, 10 mM and 20 mM in DMEM in the presence/absence of L-Ascorbic acid-2 phosphate (100 mM) (113170-55-1, Sigma-Aldrich) for 48 hours. Following treatment, the supernatant was collected and the protein level of type I collagen was measured with a procollagen type I C-peptide ELISA kit (Takara Bio Inc, Otsu, Japan). Experimental procedures followed the manufacturer's instruction. Briefly, 20 μl of culture medium and 100 μl of the antibody-POD conjugate solution were sequentially added into microtiter plates and reacted for 3 hours at 37° C. After 4× washing with washing buffer solution (1×PBST), 100 μl of the substrate solution was added and incubated for 15 minutes at RT. Finally, the stop solution (100 μl) was added and corresponding absorbance was recorded at 450 nm using a FLUOstar OPTIMA plate reader (BMG Labtech, Ortenberg, Germany).

Statistical Analysis

Data is presented as the mean±SEM. The statistical analysis was carried out using t-tests and all other analysis was performed using ANOVA, followed by Tukey's HSD post hoc test using SPSS (version 22). Microsoft Excel 2010 and Graphpad Prism v 5 was used for data handling and statistical analysis.

2. Results

In Vitro Cytotoxicity of Deferiprone

Figure 5:
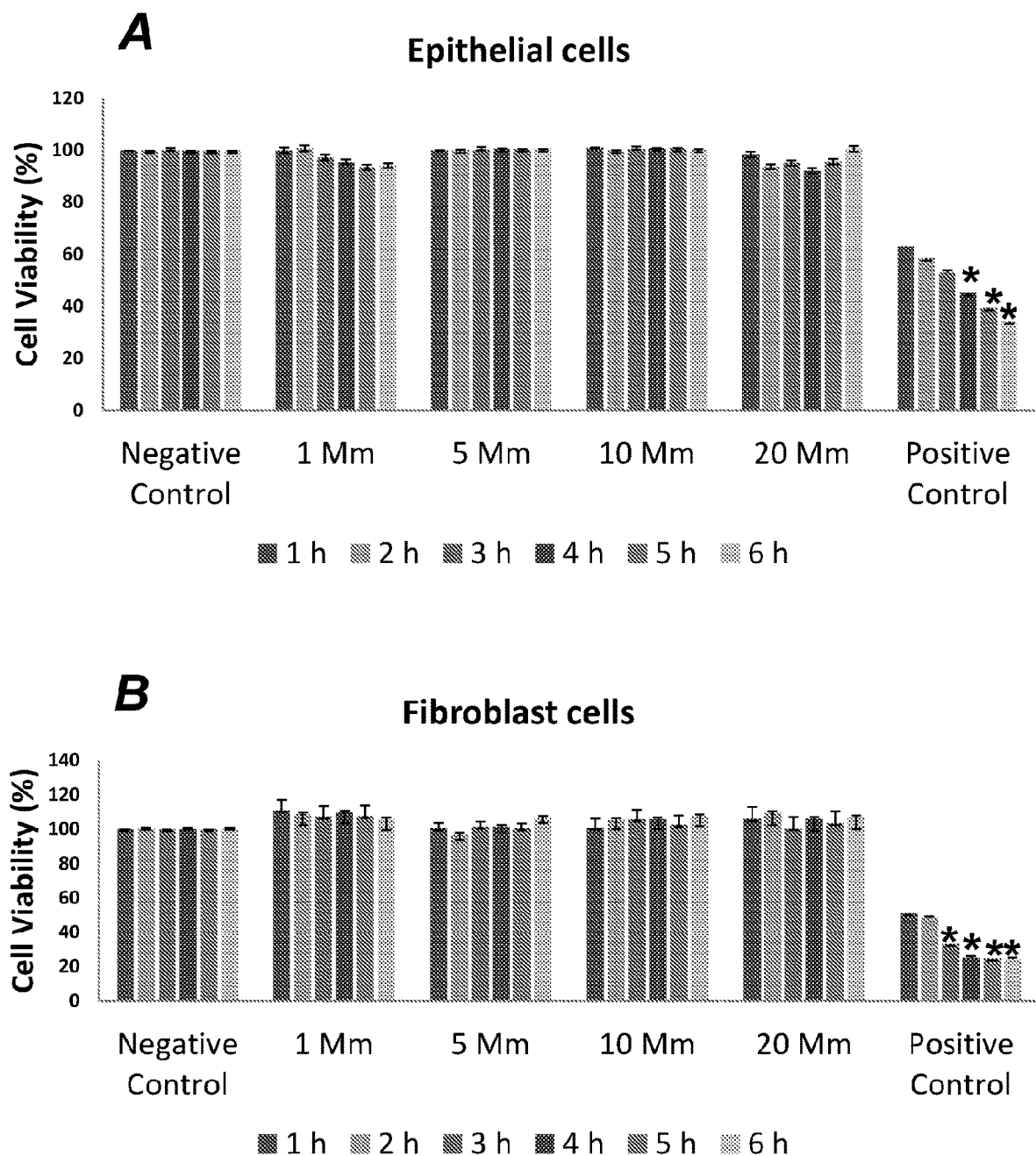
FIG. 5 shows cell viability of HNECs and human nasal fibroblast monolayers derived from CRS patients. Viability relative to no treatment control cells as determined by the LDH assay, 1 hr, 2 hr, 3 hr, 4 hr, 5 hr and 6 hours after application of deferiprone (1 mM, 5 mM, 10 mM, 20 mM), negative control (medium), and positive control (0.5% Triton X-100) in HNECs (A) and primary human nasal fibroblasts (B) derived from CRS patients. Cell viability was calculated relative to the untreated cells as negative control. The values are shown as means±SEM, n=3. ANOVA, followed by Tukey HSD post hoc test. (* p<0.05).

The cytotoxic effect of different concentrations of deferiprone (1 mM, 5 mM, 10 mM, 20 mM) was determined by the LDH assay, evaluating the survival of HNECs (FIG. 5A) and fibroblasts (FIG. 5B) over time. Different exposure times (1 h, 2 h, 3 h, 4 h, 5 h and 6 h) showed no significant increase in LDH release with any concentration of deferiprone in HNECs or fibroblasts (p>0.05). The positive control (0.5% Triton X-100) and negative control (medium) demonstrated expected toxicity values.

Effect of Deferiprone on Human Nasal Epithelial Cell and Primary Fibroblast Cell Migration In Vitro.

Figure 6:
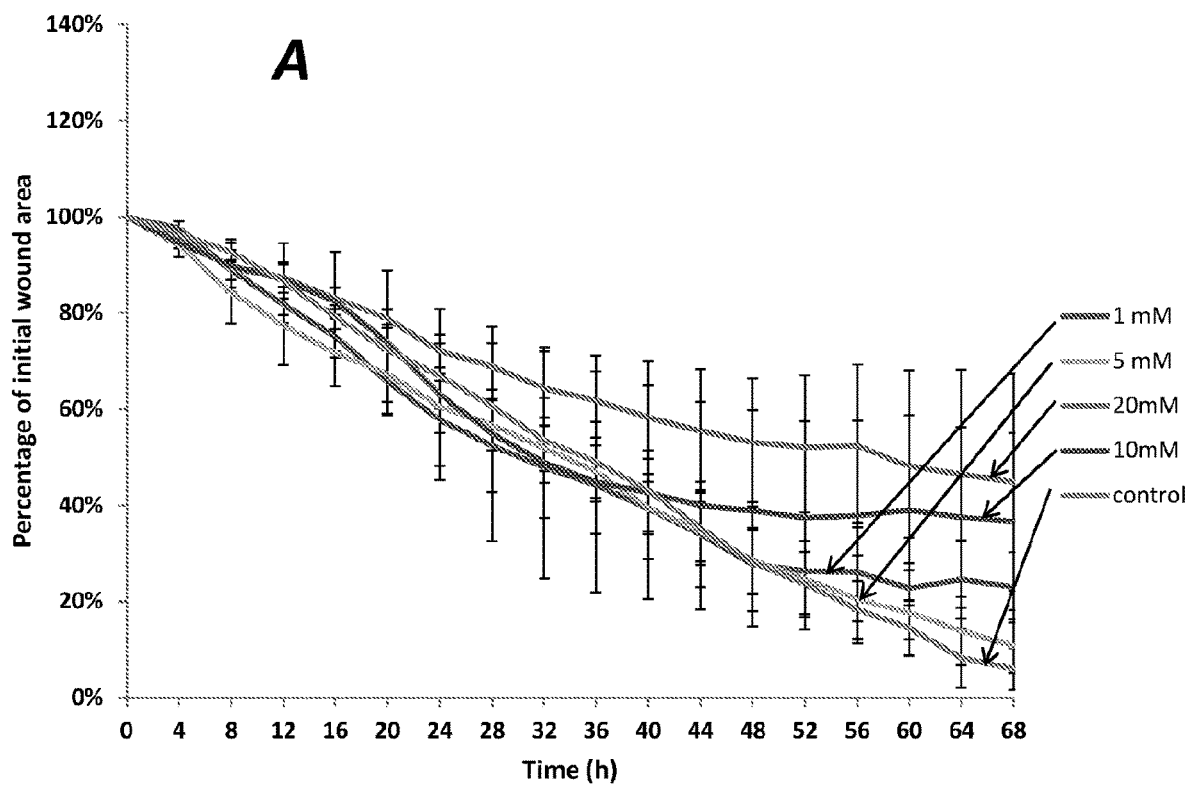
FIG. 6 shows scratch assays of primary human nasal epithelial cells and primary fibroblasts in the presence of different deferiprone concentrations over time. The mean percentage of wound area in scratch assays of primary human nasal epithelial cells (A) and sinonasal fibroblasts (B) in the presence of different concentrations of deferiprone (1 mM, 5 mM, 10 mM, 20 mM) or negative (medium) control over time. The values are shown as mean±SEM, n=3. ANOVA, followed by Tukey HSD post hoc test. * p<0.05.
Figure 6:
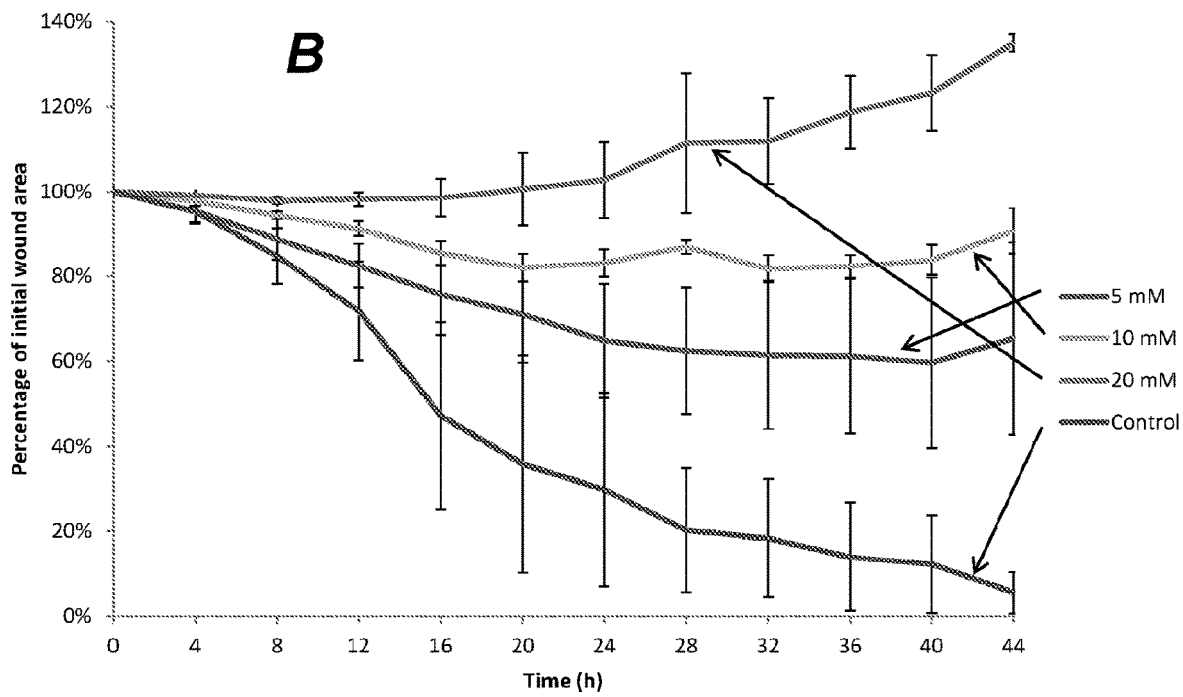

To examine the influence of deferiprone on sinonasal wound resealing in vitro, time course studies were performed during active wound closure. HNEC-ALL cultures and primary fibroblasts were treated with different concentrations of deferiprone or negative control in scratch assays. In HNEC-ALI cultures, untreated (control) wounds healed with full re-epithelialization by 68 hours. Incubation with four different concentrations of deferiprone for up to 68 hours did not show any significant delay in wound healing (FIG. 6A). Untreated primary fibroblasts closed the wound after 44 hours. Incubation with 20 mM Deferiprone caused a significant delay in wound closure at 28 h and at all time points measured thereafter. In addition, lower 10 mM and 5 mM deferiprone concentrations significantly delayed healing after 44 hours (FIG. 6B).

Figure 7:
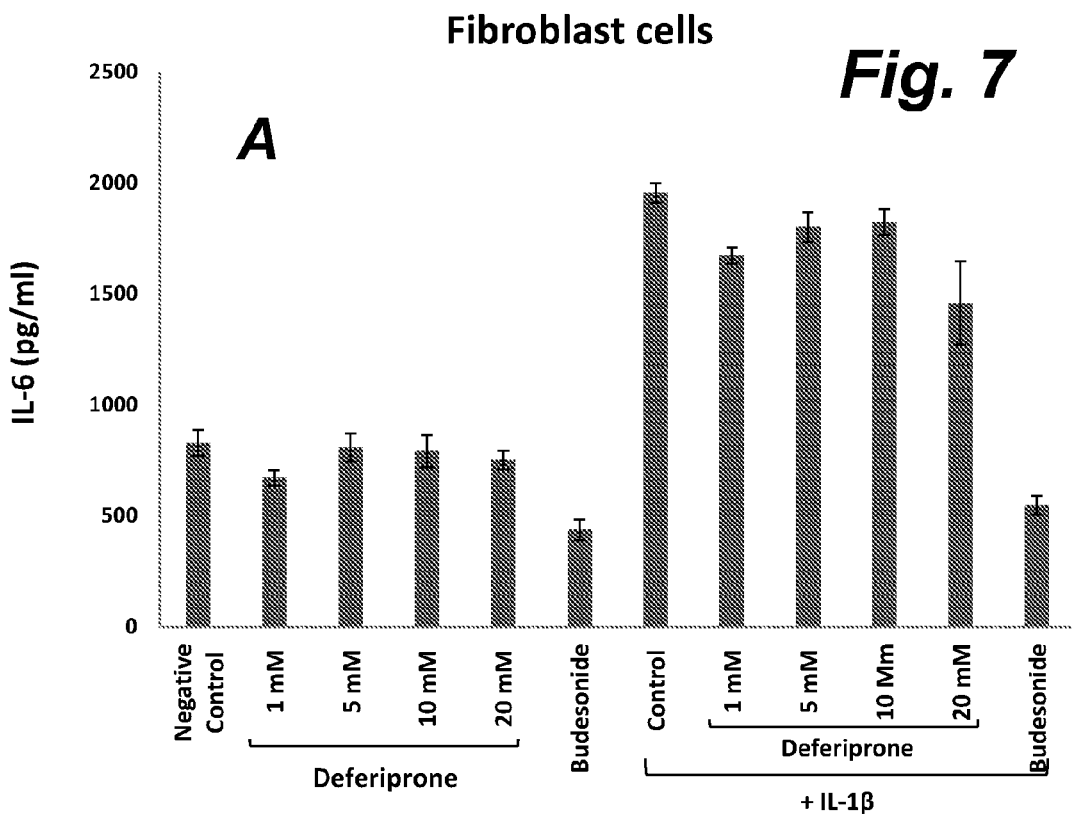
FIG. 7 shows IL-6 production was measured using ELISA on the human nasal epithelial cells (A) or nasal fibroblast cells (B) in the presence or absence of the pro-inflammatory agent Poly (I:C) or IL-1β respectively. Budesonide was used as anti-inflammatory standard of care control and medium was used as negative control. ANOVA, followed by Tukey HSD post hoc test. (*=p<0.05, =p<0.001, *=p<0.0001); values are shown as means±SEM.
Figure 7:
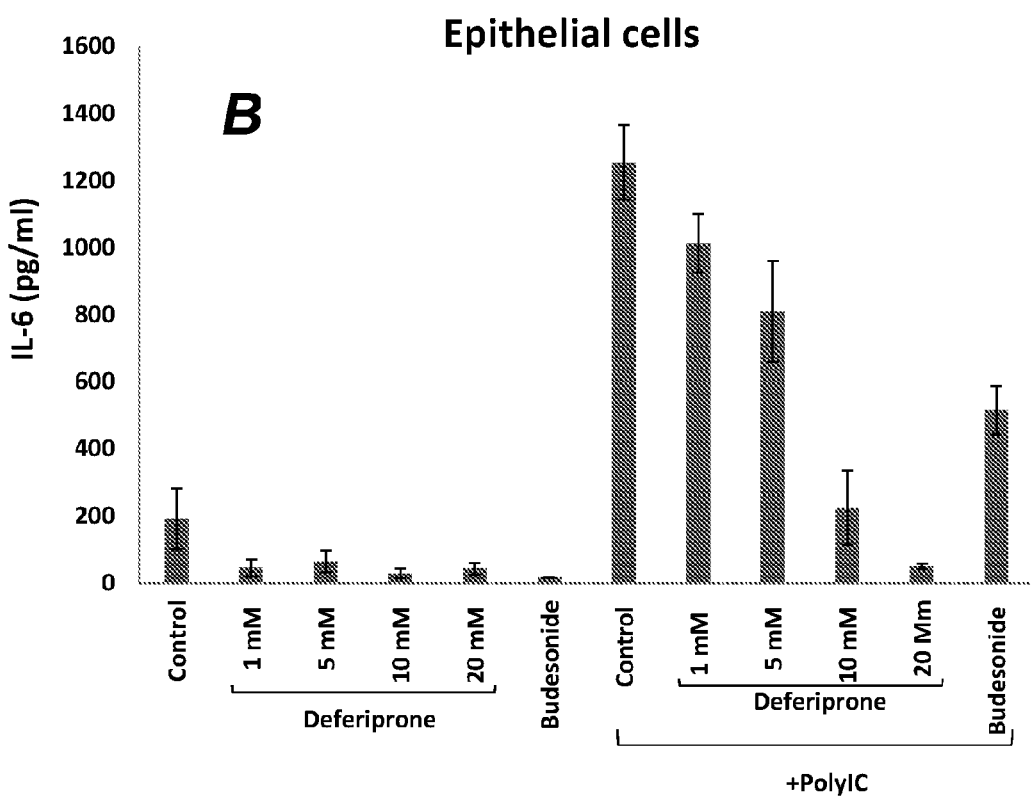

Effect of Deferiprone on Inflammatory Response in Human Nasal Epithelial Cells and Human Sinonasal Fibroblasts To determine the potential of deferiprone to dampen a pro-inflammatory response, deferiprone at different concentrations were applied to HNECs or fibroblasts in the presence or absence of the pro-inflammatory agent Poly (I:C) or IL-1β respectively. Budesonide was used as an anti-inflammatory standard of care control and significantly reduced IL-6 in both HNECs (p=0.03) and fibroblasts (p=0.001) in the presence of pro-inflammatory agents. In HNECs, application of 10 mM and 20 mM of deferiprone for 24 hours significantly reduced IL-6 protein concentrations (80% reduction, p=0.001 and 96% reduction, p=0.0001 respectively) in the presence of Poly (I:C) LMW (FIG. 7A) compared with negative control. In contrast, deferiprone did not alter the secretion of IL-6 in nasal fibroblasts in the presence or absence of IL-13 after 24 hours (FIG. 7B).

These studies indicate that deferiprone has anti-inflammatory properties, which would assist with the treatment of adhesions, particularly for the treatment of adhesions following sinus surgery.

Effect of Deferiprone on the Release of Collagen in Primary Nasal Fibroblasts

Figure 8:
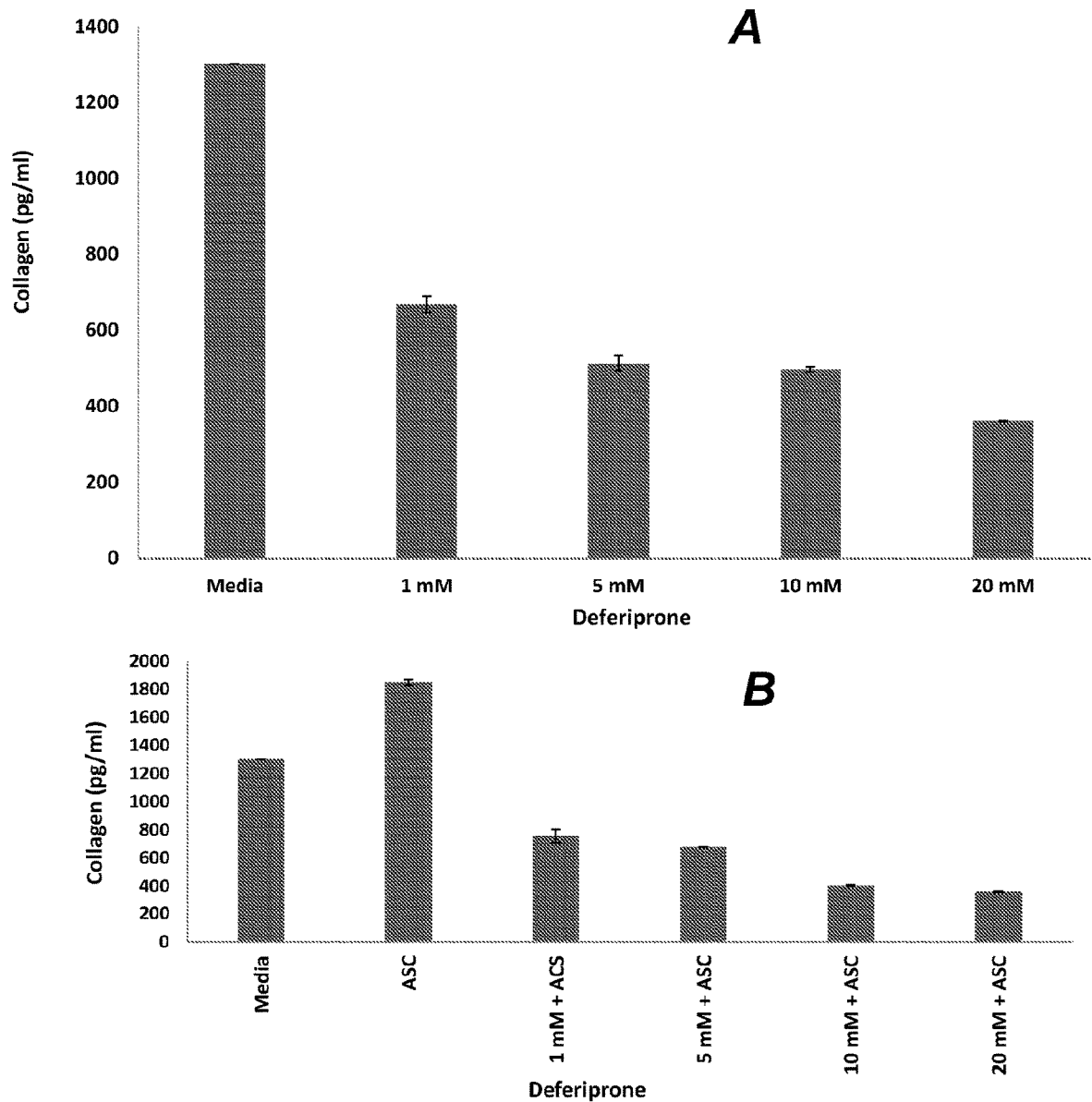
FIG. 8 shows collagen release was measured by ELISA in primary nasal fibroblasts treated with deferiprone in the absence (A) or presence (B) of L-Ascorbic acid-2 phosphate (ASC) (B). Primary human nasal fibroblasts were treated with 1 mM, 5 mM, 10 mM and 20 mM deferiprone for 48 hours. Media only and L-Ascorbic acid-2 phosphate (ASC) acted as a negative and positive control respectively. Bars stand as means±standard deviation (n=4). ( p<0.001 (* p<0.0001). ANOVA, followed by Tukey HSD post hoc test.

Application of different concentrations of deferiprone for 24 hours significantly reduced collagen protein concentrations in supernatants of fibroblast monolayers derived from CRS patients ($p<0.0001$) (FIG. 8A). In addition, deferiprone at different concentrations was applied to fibroblasts in the presence of L-Ascorbic acid-2 phosphate (ASC), known to induce collagen production by fibroblasts. Deferiprone significantly inhibited collagen secretion in a dose dependent manner in the presence ASC (FIG. 8B).

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

Although the present disclosure has been described with reference to particular examples, it will be appreciated by those skilled in the art that the disclosure may be embodied in many other forms.

The invention claimed is:

1. A method of reducing adhesions between tissue surfaces in vivo within a subject, the method comprising applying a composition to a region within the subject susceptible to formation of an adhesion between tissue surfaces, said composition comprising, as an active agent, 20 mM or less of deferiprone, wherein the deferiprone reduces adhesions in vivo within the subject.

2. The method according to claim 1, wherein the composition comprises the active agent and any one or more of a gel, a hydrogel, a solution, an emulsion, a cream, nanoparticles, microparticles, and/or liposomes.

3. The method according to claim 2, wherein the gel or hydrogel comprises one or more of a chitosan, a dextran, a carbohydrate polymer, a hyaluronic acid and/or a salt thereof, a collagen, a carboxymethylcellulose, a gelatine, a polyacylate, and an alginate.

4. The method according to claim 1, wherein the composition provides greater than 90% release of the active agent within 48 hours.

5. The method according to claim 1, wherein the composition provides a sustained release of the active agent over a period of 1 to 14 days.

6. The method according to claim 1, wherein the adhesion is an adhesion arising from a surgery.

7. The method according to claim 6, wherein the surgery comprises spinal surgery, abdominal surgery, pelvic surgery, cardiac surgery, joint and tendon surgery, sinus surgery or plastic surgery.

* * * * *